US010968381B2

(12) United States Patent
Ramírez Pérez et al.

(10) Patent No.: US 10,968,381 B2
(45) Date of Patent: Apr. 6, 2021

(54) BRANCHED GEMINAL ZWITTERIONIC LIQUIDS, METHOD FOR OBTAINING SAME AND USE THEREOF AS WETTABILITY MODIFIERS HAVING VISCOSITY REDUCING PROPERTIES

(71) Applicant: INSTITUTO MEXICANO DEL PETRÓLEO, Mexico City (MX)

(72) Inventors: Jorge Francisco Ramírez Pérez, Mexico City (MX); Raúl Hernández Altamirano, Mexico City (MX); Violeta Yasmin Mena Cervantes, Mexico City (MX); Luis Silvestre Zamudio Rivera, Mexico City (MX); Rodolfo Cisneros Dévora, Mexico City (MX); Raúl Oviedo Roa, Mexico City (MX); Ana Rocío Cartas Rosado, Mexico City (MX); Alejandro Ramírez Estrada, Mexico City (MX)

(73) Assignee: INSTITUTO MEXICANO DEL PETRÓLEO, Mexico City (MX)

( * ) Notice: Subject to any disclaimer, the term of this patent is extended or adjusted under 35 U.S.C. 154(b) by 0 days.

(21) Appl. No.: 16/907,492

(22) Filed: Jun. 22, 2020

(65) Prior Publication Data

US 2020/0317991 A1 Oct. 8, 2020

Related U.S. Application Data

(63) Continuation of application No. 15/313,545, filed as application No. PCT/MX2015/000077 on May 21, 2015, now Pat. No. 10,689,563.

(30) Foreign Application Priority Data

May 23, 2014 (MX) .................. MX/A/2014/006223

(51) Int. Cl.
*C09K 8/584* (2006.01)
*B01F 17/00* (2006.01)
(Continued)

(52) U.S. Cl.
CPC ............ *C09K 8/584* (2013.01); *B01F 17/005* (2013.01); *B01F 17/0042* (2013.01);
(Continued)

(58) Field of Classification Search
None
See application file for complete search history.

(56) References Cited

U.S. PATENT DOCUMENTS 3,643,738 A 2/1972 Dreher et al.
4,509,951 A 4/1985 Knapp
(Continued)

FOREIGN PATENT DOCUMENTS

MX 2009013704 6/2011
MX 2010012348 5/2012
(Continued)

OTHER PUBLICATIONS

International Search Report with English translation and Written Opinion for Application No. PCT/MX2015/000077 dated Sep. 8, 2015 (13 pages).
(Continued)

*Primary Examiner* — Jeffrey D Washville
(74) *Attorney, Agent, or Firm* — Casimir Jones, S.C.; Anne M. Reynolds

(57) ABSTRACT

The present invention is related with the obtaining process and use of branched germinal zwitterionic liquids based on either bis-N,N-dialkyl-N-polyether-betaine or bis-N,N-dialkenyl-N-polyether-betaine or bis-N,N-dicycloalkyl-N-polyether-betaine or bis-N,N-diaryl-N-polyether-betaine, to be applied as modifiers of the wettability of rocks such as
(Continued)

limestone, dolomite, sandstone, quartz or heteregenous lithologies, under the presence of brines having high content of divalent ions such as calcium, magnesium, barium or strontium, under high temperature and high pressure within enhanced oil recovery processes in order to increase the oil production.

The branched germinal zwitterionic liquids of the present invention have moreover the property to act as viscosity reducers of heavy oils having high content of polar fractions, both for extraction and production, and transport and storage operations, so allowing increase the production level of this oil type. An additional advantage shown by the zwitterionic liquids, derived from their molecular structure, is that they can be handed in such a manner that can be dissolved by water, hydrocarbon or other polar and non-polar solvents.

19 Claims, 9 Drawing Sheets

(51) Int. Cl.
  C07C 227/16 (2006.01)
  C07C 229/12 (2006.01)
  C07C 229/26 (2006.01)
  E21B 43/16 (2006.01)
  E21B 43/24 (2006.01)

(52) U.S. Cl.
  CPC .......... C07C 227/16 (2013.01); C07C 229/12 (2013.01); C07C 229/26 (2013.01); E21B 43/16 (2013.01); E21B 43/24 (2013.01)

(56) References Cited

U.S. PATENT DOCUMENTS

| 4,842,065 A | 6/1989 | McClure |
| 4,876,018 A | 10/1989 | Karydas |
| 5,013,462 A | 5/1991 | Danley |
| 5,042,580 A | 8/1991 | Cullick et al. |
| 5,945,393 A | 8/1999 | Tracy et al. |
| 5,952,290 A | 9/1999 | Li et al. |
| 7,041,707 B2 | 5/2006 | Hahn |
| 7,923,416 B2 | 4/2011 | Nguyen |
| 2003/0078176 A1 | 4/2003 | Elsner et al. |
| 2003/0078182 A1 | 4/2003 | Kischkel et al. |
| 2009/0023618 A1 | 1/2009 | Futterer et al. |
| 2009/0054368 A1 | 2/2009 | Wettig et al. |
| 2011/0138683 A1 | 6/2011 | Hernandez Altamirano et al. |
| 2013/0296200 A1 | 11/2013 | Hernandez Altamirano et al. |

FOREIGN PATENT DOCUMENTS

| MX | 2013007599 | 12/2014 |
| WO | WO 2005040669 | 5/2005 |
| WO | WO 2005100517 | 10/2005 |

OTHER PUBLICATIONS

Meyer et al., "Heavy Oil and Natural Bitumen—Strategic Petroleum Resources", U.S. Geological Survey (U.S. Geological Survey Fact Sheet 70-03, Aug. 2003—online version 1.0, 5 pages.

"Las reservas de hidrocarburos en Mexico (The hydrocarbon reservoirs in Mexico)" released by Petróleos Mexicanos PEMEX Exploración y Produccion 2012.

Jiang et al., "Cornucopian Cylindrical Aggregate Morphologies from Self-Assembly of Amphiphilic Triblock Copolymer in Selective Media", Journal of Physical Chemistry B, (2005), 109, 21549-21555.

Jian et al., "Density Functional Calculations, Synthesis, and Characterization of Two Novel Quadruple Hydrogen-Bonded Supramolecular Complexes", Journal of Physical Chemistry A, (2004), 108, 5258-5267.

Norrby et al., "Strong Decrease of the Benzene-Ammonium Ion Interaction upon Complexation with a Carboxylate Anion", Journal of American Chemical Society, (1999), 121, 2303-2306.

Austad, T.; Matre, B.; Milter, J.; Saevareid, A; Oyno, L. "Chemical flooding of oil reservoirs 8. Spontaneous oil expulsion from oil- and water-wet low permeable chalk material by imbibition of aqueous surfactant solutions"; J. Pet. Sci. Eng. 1998, 137, 117-129.

Standnes, D. C.; Austad, T., "Wettability alteration in chalk: 2. Mechanism forwettability alteration from oil-wet to water-wet using surfactants", Journal of Petroleum Science and Engineering, 28, (2000), pp. 123-143.

Jie et al., "Interfacial Tension Behavior of Mono-Isomeric Phenyltetradecane Sultanates", Energy Sources, (2005), 27, 1013-1018.

Badger et al. (Badger M. W.; Schobert, H. "Viscosity Reduction in Extra Heavy Crude Oils" Carbon, vol. 1, p. 461-465.

Garcia-Martinez; J.; Tesis de Maestrfa. 2004; Una aproximación a la estructuramolecular de asfaltenos separados de aceites crudos mexicanos; Facultad deEstudios Superiores Cuautitlan de la Universidad Nacional Autonoma de Mexico; Mexico.

250 ppm 500 ppm 1000 ppm (6) General structure of a branched geminal zwitterionic liquid.

(7) General structure of a branched geminal zwitterionic liquid based on bis-N,N-dialkyl-N-polyether-betaine or bis-N,N-dialkenyl-N-polyether-betaine or bis-N,N-dicycloalkyl-N-polyether-betaine or bis-N,N-diaryl-N-polyether-betaine (8) 1) Chemical structure of the asphaltene, 2) calcite surface, and 3) the asphaltene adsorbed on the calcite surface.

(9) 1) Chemical structure of the asphaltene, 4) dolomite surface, and 5) the asphaltene adsorbed on the dolomite surface.

(10) 6) Chemical structure of the branched geminal zwitterionic liquid, 2) calcite surface, and 7) branched geminal zwitterionic liquid adsorbed.

(11) 6) Chemical structure of the zwitterionic liquid, 4) dolomite surface, and 8) branched geminal zwitterionic liquid adsorbed.

(12) 1) Asphaltene molecular structure, 1) asphaltene molecular structure, and 9) aggregation between the two asphaltene molecular structures.

BRANCHED GEMINAL ZWITTERIONIC LIQUIDS, METHOD FOR OBTAINING SAME AND USE THEREOF AS WETTABILITY MODIFIERS HAVING VISCOSITY REDUCING PROPERTIES

CROSS-REFERENCE TO RELATED APPLICATIONS

The present application is a continuation of U.S. patent application Ser. No. 15/313,545, filed Nov. 22, 2016, allowed as U.S. Pat. No. 10,689,563, which is a U.S. national stage entry of International Patent Application No. PCT/MX2015/000077, filed on May 21, 2015, which claims priority to Mexican Patent Application No. MX/a/2014/006223, filed on May 23, 2014, the entire contents of all of which are fully incorporated herein by reference.

DESCRIPTION

Technical Field of the Invention

The present invention lies within the field of multifunctional chemicals applied to the oil industry for the enhanced oil recovery processes; specifically, describes the obtaining and use of branched geminal zwitterionic liquids with wettability modifying properties on carbonate rocks and heterogeneous lithologies under presence of brines having a high concentration of divalent ions such as calcium, magnesium, barium and strontium, and under high temperature and high pressure.

The branched geminal zwitterionic liquids of the present invention have moreover the property to act as viscosity reducers for polar-fractions-high containing heavy oils, both in extraction and production as well as in transport and storage operations, allowing so to increase the production levels of this oil type.

BACKGROUND OF THE INVENTION

Zwitterionic liquids are compounds that although being electrically neutral, contain positive (cation) and negative (anion) formal charges at different atoms of the same molecule, giving them the characteristic to behave either as acids or bases (donors or acceptors) depending on the characteristics of the medium in which they are lying. They are molecules capable of adapting to different media and therefore can be designed to respond in an effective way depending on contaminants and operating conditions where they are applied.

Below it is shown some examples of chemical structures of zwitterionic liquids that are reported in the literature (1):

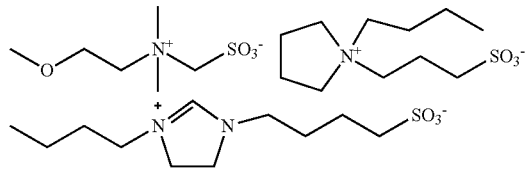

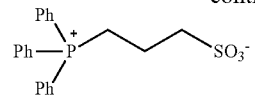

(1) Chemical Structures of Some Zwitterionic Liquids

For the particular case of the increase in the production of hydrocarbons, it is found that after primary and secondary recoveries the oil field contains still 50-80% of the original crude oil in place. This is due to that the efficiency of primary and secondary recovery methods is limited by two factors:

On the pore scale, the crude oil can reach a residual saturation sufficiently low to be found in the form of discontinuous globules, which are trapped by capillary forces.

On the reservoir scale, there are certain zones through which the fluid injected during the secondary recovery does not penetrate due to the low permeability of these zones.

The currently proposed enhanced oil recovery methods are aimed to the solution of the above mentioned problems. For this purpose, the use of wettability-modifier surfactants chemicals is one of the most widely used methods; within them it is find cationic, anionic, non-ionic and zwitterionic surfactants or mixture thereof.

A wettability modifier is defined as a surfactant able to change favorably the reservoir-rock affinity. The wettability is a measure of the interaction between the phases present in the reservoir and is a function of the interfacial chemistry of those phases, and determines the tendency of a fluid to advance or to adhere onto a solid surface under the presence of other immiscible fluids. The rock wettability can be naturally modified by the adsorption of polar compounds, the deposits formation of material organic which originally stayed in the oil, or by external agents. Wettability changes affect the capillary pressure, the relative permeabilities, the residual-oil saturation and the irreducible-water saturation.

Despite the continuing advances in the development of wettability-modifiers chemicals, currently in Mexico there exist reservoirs which are very difficult to treat due mainly to they are naturally fractured, have low permeability, show heterogeneous lithologies, high temperatures (above 90° C.) and a high salinity usually greater than 60,000 ppm as sodium chloride and a high content of divalent ions (calcium and magnesium, greater than 5,000 ppm).

Due to the above factors, the characterization of the rock type from which the reservoir is formed, as well as of the composition of both the adsorbed crude oil and the medium surrounding it, is paramount for designing new wettability modifiers in order to propose molecular structures that are tolerable to brines saturated by salts of mainly calcium and magnesium, have good diffusion through the medium which is generally composed of brine-oil mixtures, and have polar groups with affinity for the rock to favorably change the rock wettability from oil wet to water wet.

Worldwide, there are a variety of specific cases of chemicals that have been successfully used to solve above problems, within which there are anionic surfactants, such as sodium alkyl sulfonates, or cationic surfactants, such as alkyl ammonium chlorides, but unfortunately their application is not universal since the conditions that are present in Mexican reservoirs are quite different from those that are found in other countries; then, it becomes paramount the development of more versatile chemicals that can be used in increasingly adverse conditions and, moreover, can simultaneously solve the greatest number of problems, such as for example the corrosion that it is found directly associated to the use of sea water or connate water, which are normally used as means of transport for the wettability-modifier chemical to be injected into the oil field in order to minimize the costs of its implementation.

In order to increase the oil-recovery factor, it have been developed wettability-modifiers chemicals such as the ones mentioned below:

U.S. Pat. No. 5,042,580 (Oil Recovery Process for its use in Fractured Reservoirs) protects an enhanced oil recovery process that involves injecting in the reservoir a wettability modifier composed of a mixture of different types of alkyl-sulfonate surfactants and chrome salts derived from fatty carboxylic acids.

U.S. Pat. No. 4,509,951 (Enhanced Recovery through Imbibition Processes) protects an enhanced recovery process that involves injecting in the reservoir a wettability modifier composed of a mixture of different types of chemicals, within which there are ammonium salts, alkali metals hydroxides, alkyl tripolyphosphates and carbonates and bicarbonates of alkali metals.

U.S. Patent Application No. 2009/0023618 A1 (Method for Oil Recovery) protects an enhanced recovery process that involves injecting into the reservoir a wettability modifier composed of a mixture of different types of organophosphorus-based compounds.

U.S. Pat. No. 4,842,065 (Oil Recovery Process using a Cyclic Process for the Alteration of Wettability) protects an enhanced recovery process that involves injecting into the reservoir a wettability modifier composed of a mixture of different types of ethoxylates alcohols.

U.S. Pat. No. 3,643,738 (Wettability Control in Oil Recovery Processes) protects a process that allows to control the wettability change through the use of mixtures of petroleum sulfonates.

Surfactants of germinal type constitute a family characterized by possessing at its molecules at least two hydrocarbon chains and two hydrophilic or polar groups, whereas the molecules of conventional surfactants contain one or two hydrocarbon chains attached to a same polar group.

Most of geminal surfactants have in their molecules a hydrocarbon chain, a polar group, a short hydrocarbon chain that acts as a bridge, a second polar group and other hydrocarbon chain.

The first synthesis of germinal surfactants was announced in 1971 by C. A. Bunton, L. Robinson, J. Schaak and M. F. Stam from the California University, who called them dicationic detergents. These researchers used cationic geminal surfactants as catalysts for certain nucleophilic substitution reactions. The successive names taken by these substances were: quaternary bis-ammonnium surfactants, dimeric surfactants, geminals or gemini (from Latin) surfactants and siamese surfactants.

For the most part of geminal surfactants, the polar groups are ionic (cationic, anionic, and less frequently, amphoteric), but it was also synthesized surfactants having non-ionic polar groups formed by polyethers. At pioneer work of Bunton, Robinson, Schaak and Stam, the short hydrocarbon chain that acts as a bridge was named bridging group since it joins the two surfactant parts, each of which consists of a polar group, in this case a cation, and a lipophilic chain.

As representative examples of processes for obtaining new geminal surfactants, it is had the below patent-document references:

U.S. Pat. No. 5,945,393 (A), published on Aug. 31, 1999, relates with obtaining gemini non-ionic surfactants based on either alkyl phosphonates or sulfonates or alkyl-aryl polyethers, and their application in the formulation of detergents and chemicals for the personal hygiene.

U.S. Pat. No. 5,952,290 (A), published on Sep. 14, 1999, relates with obtaining gemini anionic surfactants based on either alkyl amides or alkyl-aryl sulfonates, and their application in the formulation of detergents and chemicals for personal hygiene.

U.S. Pat. No. 2003/078176 (A1), published on Apr. 24, 2003, relates with obtaining surfactants based on long-chain alcohols and ethylene oxide-derived polyethers, and their application in detergents formulation.

U.S. Pat. No. 2003/078182 (A1), published on Apr. 24, 2003, relates with obtaining compositions of gemini surfactants based on 1,2-epoxy-alkane, where the alkyl groups may be linear or branched, and ethylene oxide-derived polyols, and their application in detergents formulation.

U.S. Pat. No. 2009/054368 (A1), published on Feb. 26, 2009, relates with obtaining quaternary amines-based gemini surfactants substituted by alkyl or aryl groups such as the pyrene, and their application in the controlled release of active biological agents such as nucleic acids.

Patent application No. MX/a/2010/012348 A refers to a composition based on geminal zwitterionic liquids to act as wettability modifiers in enhanced oil recovery processes. It is worth to mention that the zwitterionic liquids of such patent application differ from the present invention since they are not branched type.

The effect of branching tensoactive agents is reported in the scientific article called "Interfacial Tension Behavior of Mono-Isomeric Phenyltetradecane Sulfonates" (Energy Sources 2005, 27, 1013-1018) which mentions that the surface tension of a system can be modified through manipulating the molecular structure of the surfactants, and that in chain-containing isomers, the surface tension decreases as it is reached a symmetry at the branches (3). The foregoing leads to that symmetrical branching at geminal zwitterionic liquids improves the wettability-modifier performance relative to not-branched structures since they generate an effect of reducing the interfacial tension.

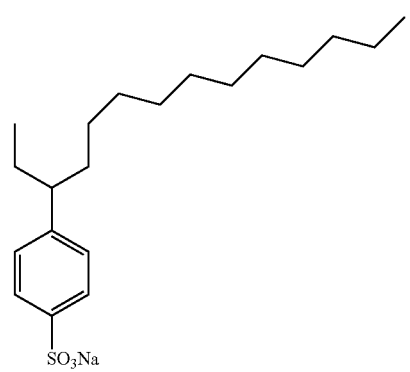

0.1 mN/m

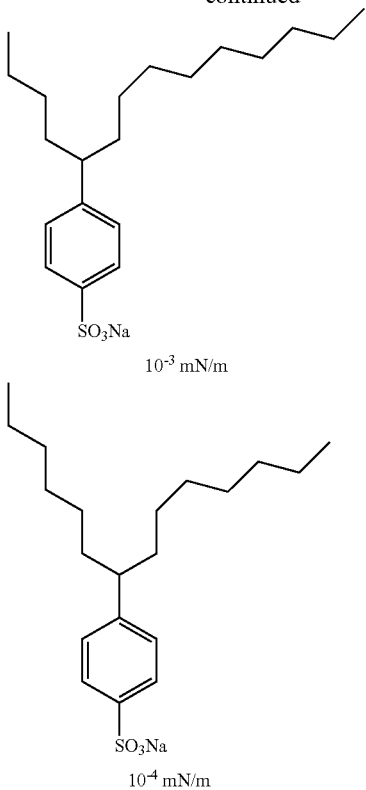

$10^{-3}$ mN/m $10^{-4}$ mN/m (2). Interfacial Tension Modification as Function of the Structural Characteristics of Sodium Alkylbenzenesulfonates On the other hand, in the oil industry throughout its productive chain there are several issues daily causing millions of dollars losses due to falls in the production or in the efficiency of the oil transportation processes. One of these issues is related to high viscosity shown by oils having a high content of high-molecular-weight polar fractions, such as asphaltenes and resins. These polar fractions are integrated by high-molecular-weight molecules containing in their structure heteroatoms such as nitrogen, oxygen and sulphur, whose intermolecular forces are able to generate interactions of higher energy, such as hydrogen bridges or dipole-dipole interactions, than the low polarity of low-molecular-weight fractions, leading to a significant increase of the viscosity shown at macroscopic level. The larger the content of this type of fractions is in the crude oil, the increase in the viscosity of the latter will be greater. Therefore, the exploitation of heavy-oil-containing reservoirs represents both a technological challenge and a costs increase relative to the conventional-light-oils-containing reservoirs.

According to a report from the U.S. Geological Survey (U.S. Geological Survey Fact Sheet 70-03, August 2003—online version 1.0), it has been determined that worldwide the volume of heavy and extra-heavy oil reserves which are technically feasible to exploit rises to 434.3 billion barrels preferentially concentrated in the regions of South America, Middle East, North America and Asia.

In Mexico, according to the document "Las reservas de hidrocarburos en México (The hydrocarbon reservoirs in Mexico)" released by Petróleos Mexicanos (PEMEX Exploración y Producción 2012), the heavy, light and super-light oils contribute 52.4, 35.3 and 12.4 percent, respectively, to the total crude-oil reserves of the nation.

Based on above numbers, it can be appreciated the importance of technologies aimed to increase the technical feasibility and to reduce the costs for the exploitation and processing of heavy and extra-heavy oils, taking into account the high oil-reserve volume available around the world.

The extraction and transportation of crude oil and oil-derived products having high viscosity constitutes a great technological challenge for the oil industry. Historically, it has been used several techniques to facilitate the extraction of high-viscosity crude oil as well as to facilitate their transportation from production sites to the storage or processing plants. The heavy oils show viscosities usually found in the range from 10,000 to 500,000 cP at room temperature. As a result, it is required the implementation of special-pumping and heating stations to maintain a low viscosity, making possible to perform the transport of this oil type through pipelines. Some of these techniques, such as the mechanical pumping assisted by steam injection or the use of insulation and supply of heat at pipelines, show obvious disadvantages and limitations in their implementation, impacting negatively on the economy of production of this oil type; among these, one can quote the low volumetric efficiency of pumping and the increase in energy consumption per produced barrel, etc.

It has been recently appealed to the addition of viscosity-reducers chemical agents in order to improve the profitability of the exploitation and processing of this petroliferous type.

As representative examples of viscosity-reducers agents for heavy oils, it is had the following references of patent documents:

WO/2005/100517(A1) published on Oct. 27, 2005. It describes a method for reducing the crude-oil viscosity through the introduction of additives based on polyvinyl alcohols (PVA). These additives must be added in amounts ranging from 10 to 40% mixing or dispersion volume. This type of technologies shows the disadvantage of requiring high additive concentrations to achieve the reducing-viscosity effect; moreover, the additives must be diluted in aqueous solvents causing emulsions that should be broken in subsequent operations, representing an increase in costs.

U.S. Pat. No. 5,013,462 published on Mar. 7, 1990. It refers to methods for improving the mobility and productivity of viscous crude oils through the formation of an oil-in-water emulsion composed of oil and from 20 to 80 wt % water in the presence of 100 to 1,500 weight parts per million of a tensoactive mixture. The used tensoactive mixture consists of an anionic tensoactive or amphoter, A, selected between an ethoxylated aryl sulfonic acid base, A1, an aryl sulfonic acid base, A2, or an imidazoline quaternary base, A3, whose structural formula is shown in (4), or sodium or ammonium salts themselves, and a non-ionic tensoactive selected between an aryl polyethylene glycol or a copolymer derived from ethylene oxide, B, and propylene oxide, C, shown in (5).

A1

Ar(OCH$_2$CH$_2$)$_n$OSO$_3$H

A2

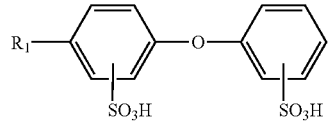

-continued

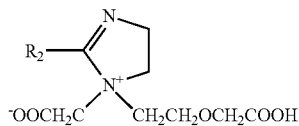

A3

(3) Structures of Anionic Surfactants and Amphoters Protected by U.S. Pat. No. 5,013,462

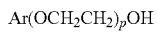

B

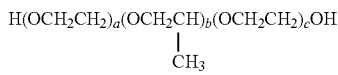

C (4) Structures of Non-Ionic Surfactants Protected by the U.S. Pat. No. 5,013,462

U.S. Pat. No. 7,923,416 (B2), published on 12 Apr. 2011. It divulges a method to reduce the viscosity of hydrocarbon fluids. The method consists in to form a low-viscosity emulsion by mixing the liquid hydrocarbon with an effective amount of a water-soluble polymer containing pendant methyl ether-type groups, as shown in (6). This technology was compared with anionic surfactants similar to the ones divulged in U.S. Pat. No. 7,041,707 B2, and against commercial products based on PVA similar to the ones reported in WO2005/040669 A1, finding that the methyl ether-groups-containing water-soluble polymers are comparable or superior in efficiency relative to the above technologies.

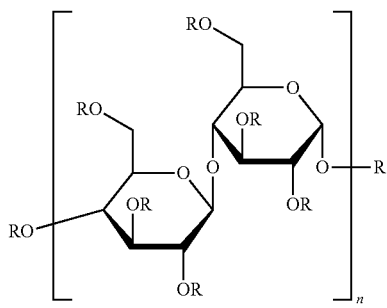

(5) Structure of the water-soluble polymer shown in the patent application U.S. Pat. No. 7,923,416 (B2).

However, both this technology and the above mentioned ones show the disadvantage of reducing the crude-oil viscosity through the formation of emulsions that will later have to be broken.

U.S. Pat. No. 4,876,018, published on Jan. 19, 1988. It describes a method to reduce the asfaltenic-crude-oils viscosity in pumping or transportation operations through the incorporation of a quantity of an oil-soluble organic compound having at least one fluor-aliphatic-oleophobic and hydrophobic group and, optionally, a low-viscosity solvent, as well as compositions of the same. These technologies require low concentrations of additives but their efficiencies demonstrated efficiencies under 20% reduction in oils of 360 cP at 25° C. and their maximum test temperature was 50° C. Also, it is found reported in the specialized literature that even at low concentrations, the fluorinated compounds cause poisoning problems to catalysts and additives in refining processes, so the incorporation of them to crude oil would be not desirable.

Along to the above aspects, the trend worldwide in the field of chemical products is the development of multifunctional chemicals, that is, products whose active ingredient possesses a chemical structure designed to present more than one functionality in order to control various problems arising in some process or operations of the industry. The design and application of multifunctional chemicals eliminates problems of incompatibility that occurs by the simultaneous use of different chemical also, represents an alternative that reduces costs relative to conventional combination technologies consisting in combining chemicals.

Regarding the molecular design of branched geminal zwitterionic liquids, an important design stage is the use of supramolecular chemistry, which is defined as the chemistry that deals with the study of systems involving aggregates of molecules or ions that are joined through non-covalent interactions, such as electrostatic interactions, hydrogen bridges, π-π interactions, dispersion interactions and solvophobic effects. The supramolecular chemistry can be divided into two large areas: 1) Host-Guest Chemistry and 2) Self-assembling. The difference between these two areas is a matter of size and shape; where there is no significant difference in size and none of the species acts as host for the other, the non-covalent binding between two or more species is called self-assembling.

From the energy view point, the supramolecular interactions are much weaker than the covalent interactions, which are located in the energy range from 150 to 450 kJ/mol for simple bonds. The energy range of the non-covalent interactions is located from 2 kJ/mol for dispersion interactions until 300 kJ/mol for ion-ion interactions (Table 1). The sum of several supramolecular interactions can give rise to highly stable supramolecular complexes.

TABLE 1

| Strength of supramolecular interactions | |
|---|---|
| Interaction | Force (kJ/mol) |
| Ion-ion | 200-300 |
| Ion-dipole | 50-200 |
| Dipole-dipole | 5-50 |
| Hydrogen bridge | 4-120 |
| π Cation | 5-80 |
| π-π | 0-50 |
| Van der Waals | <5 |
| Hydrophobic | related to the solvent-solvent interaction energy |

Based on the above background, in the present invention we make use of the computational chemistry which is a tool widely used worldwide to predict the stability and structure of chemical systems with potential improved properties, and has found application at industrial level in the development of studies for the quantitative structure-activity relationship. Within the computer calculation methods that have been used for this purpose, it is found the molecular mechanics methods, the quantum methods, which comprise the semiempirical and ab initio methods, and the density-functional-theory methods. As examples from the literature that demonstrate the use of computational chemistry to predict accurately supramolecular interactions in chemical systems, and/or thermodynamic and kinetic aspects of chemical processes, it can be mentioned the articles entitled: 1) Cornucopian Cylindrical Aggregate Morphologies from Self-Assembly of Amphiphilic Triblock Copolymer in Selective Media (*Journal of Physical Chemistry B*, 2005, 109, 21549-21555), 2) Density Functional Calculations, Synthesis, and Characterization of Two Novel Quadruple Hydrogen-Bonded Supramolecular Complexes (*Journal of Physical Chemistry A*, 2004, 108, 5258-5267), and 3) Strong Decrease of the Benzene-Ammonium Ion Interaction upon Complexation with a Carboxylate Anion (*Journal of American Chemical Society*, 1999, 121, 2303-2306).

It is important to emphasize that in none of the above references it was talked about obtaining and using branched geminal zwitterionic liquids of type either bis-N,N-dialkyl-N-polyether-betaine or bis-N,N-dialkenyl-N-polyether-betaine or bis-N, N-dicycloalkyl-N-polyether-betaine or bis-N,N-diaryl-N-polyether-betaine, nor suggested their obtaining process, nor their use as wettability modifiers having viscosity reducers properties, which favorably alter the rock wettability in enhanced crude-oil recovery processes on a wide variety of rocks such as limestone, dolomite, sandstone, quartz or heterogeneous lithologies, nor they may be exposed to brines with high content of divalent ions such as calcium, magnesium, barium and strontium (150,000 ppm), temperatures up to 220° C. and pressures up to 300 kg/cm$^2$, nor they reduce the viscosity of heavy oils containing a large proportion of high-molecular-weight polar molecules, such as asphaltenes and resins, with the purpose in both cases to increase the recovery factor of the remaining oil stored in the reservoir under conditions of high temperature and high salinity, nor these branched geminal zwitterionic liquids are designed by using computational chemistry tools based on supramolecular-chemistry knowledges in order to obtain optimized structures for the application to which they are addressed.

BRIEF DESCRIPTION OF THE DRAWINGS OF THE INVENTION

This patent or application file contains at least one drawing executed in color. Copies of this patent or patent application publication with color drawing(s) will be provided by the Office upon request and payment of the necessary fee.

DETAILED DESCRIPTION OF THE INVENTION

The present invention is related with the obtaining and the usage of branched gemini zwitterionic liquids based on either bis-N,N-dialkyl-N-polyether-betaine or bis-N,N-dialkenyl-N-polyether-betaine or bis-N,N-dicycloalkyl-N-polyether-betaine or bis-N,N-diaryl-N-polyether-betaine to be applied as wettability modifiers for rocks such as limestone, dolomite, sandstone, quartz or heterogeneous lithologies under the presence of brines having high content of divalent ions such as calcium, magnesium, barium and strontium, high temperature and high pressure, all above in order to increase the oil production.

The branched geminal zwitterionic liquids of the present invention have moreover the property to act as viscosity reducers for heavy oils possessing high content of polar fractions, in both extraction and production as well as transport and storage operations, so allowing to increase the production level of this type of oils. An additional advantage shown by the zwitterionic liquids, and derived from their molecular structure, is that they can be manipulated in such a way that its partition coefficient allows them to be soluble in either water, hydrocarbons or both systems.

Figure 3:
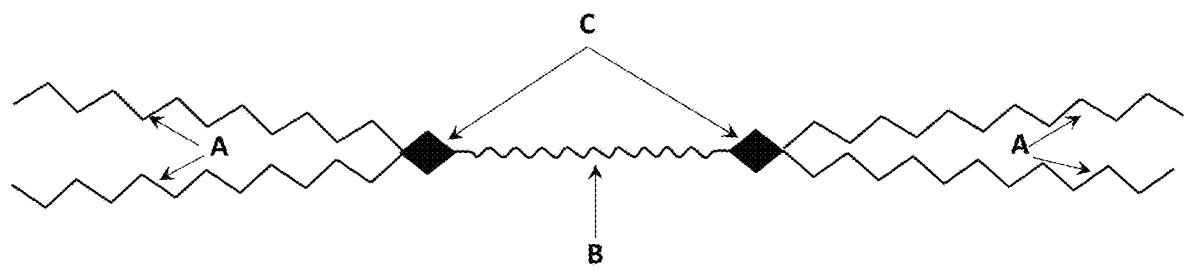
FIG. 3 shows the general structure of a branched geminal zwitterionic liquid.

The branched geminal zwitterionic liquids (6) of the present invention are a family characterized by possessing four hydrocarbon chains, which can be the same or different in size (A), a polyether-type bridge (B) and two polar zwitterionic-type groups based on betaine (C), as illustrated in FIG. 3.

Figure 4:
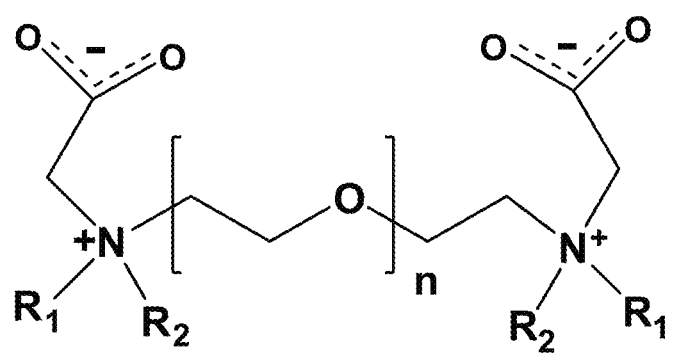
FIG. 4 shows the general structure of a branched geminal zwitterionic liquid based on bis-N, N-dialkyl-N-polyether-betaine or bis-N, N-dialkenyl-N-polyether-betaine or bis-N, N-dicycloalkyl-N-polyether-betaine or bis-N, N-diaryl-N-polyether-betaine.

The new branched geminal zwitterionic liquids surfactants based on either bis-N,N-dialkyl-N-polyether-betaine or bis-N,N-dialkenyl-N-polyether-betaine or Bis-N,N-dicycloalkyl-N-polyether-betaine or bis-N,N-diaryl-N-polyether-betaine (7), of the present invention, have the structural formula shown in FIG. 4, where:

$R_1$ is an alkyl or alkenyl, linear or branched chain, preferably having 1 to 30 carbon atoms; or instead a cycloalkyl or aryl group, preferably having 5 to 12 carbon atoms;

$R_2$ is an alkyl or alkenyl, linear or branched chain, preferably having 1 to 30 carbon atoms; or instead a cycloalkyl or aryl group, preferably having 5 to 12 carbon atoms.

The label n can have values from 1 to 500, depending on the molecular weight of the used polyether, which is derived from ethylene oxide and its molecular weight is found in the range 100 to 22,000 g/mol.

For the development of the present invention it was followed a procedure consisting of the following stages: 1) molecular design through computational chemistry, 2) synthesis of branched geminal zwitterionic liquids, 3) spectroscopic characterization of the branched geminal zwitterionic liquids and 4) experimental evaluation of the rock-wettability-modifier and heavy-oil-viscosity-reduction properties. The selection of the current methodology is based on the fact that the dot key to solve the problem to develop agents having wettability-modifier and viscosity-reduction properties, being high-salinity and divalent-ions-concentration tolerant, and being able to withstand high-temperature and high-pressure conditions, is the understanding at molecular level of the mechanism: 1) for generate ion-dipole or ion-ion pairs between the wettability-modifier agent and the oil polar compounds, and for be capable to alter the carbonate-rock wettability from oil-wet to water-wet under conditions of high divalent-ions concentration, which increase the potential for either precipitation or phases separation when the traditional surfactants are used, and 2) simultaneously, for these ion-dipole interactions to help the breaking of the hydrogen-bridge and dipole-dipole interactions there are between high-molecular-weight polar-fractions molecules lying in the oil and that cause the high oil viscosity. An additional advantage shown by the branched geminal zwitterionic liquids, derived from their molecular structure, is that they can be manipulated in such a way that their partition coefficient allows them to be soluble in either water, hydrocarbons or both systems.

1) Molecular Design by Means of Computational Chemistry

In the sake of simplicity and before going into details, it is convenient to mention that the current worldwide trend of the process involving the development of chemicals to be applicatied at industrial level has as the first stage the design, by means of computational chemistry, of the molecules that will have the potential ability to solve the problem of interest. Such molecular design is intended to systematically direct the efforts aimed to the synthesis of new molecules having new enhanced properties.

For the specific problem of wettability modification and viscosity reduction in heavy oils, the first thing to determine in the molecular design is:

i) The magnitudes of the interaction forces existing between the rock surface characteristic of a given reservoir and the high-molecular-weight crude-oil polar molecules, since these data constitute the reference energy that must be overcome by the insertion of an appropriate wettability-modifier agent.

ii) Also, it is required to understand the mechanisms on which the wettability change is based in order to propose a surfactant having the most appropriate molecular structure.

iii) In addition, for the viscosity-reduction application, it is required to determine the nature and magnitude of the intermolecular forces generating the high viscosity in oils having a high content of high-molecular-weight polar compounds such as the asphaltenes and resins. These data provide the reference energy that must be overcome by the insertion of an appropriate viscosity-reducer agent.

iv) Finally, optimal structural parameters a wettability-modifier and viscosity-reducer molecule must include are selected from the technical-economic viewpoint in order to propose an initial molecular structure to which it is calculated the interaction energy with the rock surface to determine whether this interaction will be a greater or lesser energy with respect to those of the high-molecular-weight polar organic compounds which are required to remove from the surface so as to increase the oil recovery factor of the reservoir. At this point, the process can be iterative until find a molecule that effectively does have an interaction energy with the rock greater than those of the absorbed oil polar compounds.

At the specialized literature it is mentioned that the effectiveness of the rock-wettability change depends on the ionic nature of the involved surfactant (Colloids Surf. A: Physicochem. Eng. Aspects 1998, 137, 117-129. Austad, T.; Matre, B.; Milter, J.; Saevareid, A.; Oyno, L. *Chemical flooding of oil reservoirs* 8. *Spontaneous oil expulsion from oil- and water-wet low permeable chalk material by imbibition of aqueous surfactant solutions*; J. Pet. Sci. Eng. 2000, 28, 123-143. Standnes, D. C.; Austad, T. *Wettability alteration in chalk: 2. Mechanism for wettability alteration from oil-wet to water-wet using surfactants*) and that in oil-wett limestone cores, the cationic surfactants show a better performance than the anionic ones. It has been proposed that in the case of cationic surfactants, the mechanism through which they modify the wettability in an oil-wet rock is by the formation of ionic pairs between the surfactant cationic heads and the oil acidic components found adsorbed on the carbonate rock surface.

The formation of this ionic pairs could remove from the rock surface the adsorbed layer of crude oil components, thus exposing the calcium-carbonate rock surface, which is water-wet in origin. In contrast, the anionic surfactants would form a monolayer on the rock surface through a hydrophobic interaction between the tails of the surfactant molecules and the crude oil components adsorbed on the rock surface. At this way, the rock would be covered by a surfactant-molecules layer formed with hydrophilic groups on the surface, which could modify the rock-wettability characteristics, from oil-wet to more water-wet.

In the case of the present invention, the zwitterionic surfactants would have the ability to alter the carbonate-rock wettability from oil-wet to water-wet through the two above mentioned mechanisms in parallel and thus would present a greater efficiency than the cationic or anionic surfactants they have been traditionally used.

Moreover, the charge duality shown in their structure would allow them interact effectively with different rock and oil types, since they could form ionic pairs with species possessing both positive and negative charges.

As it was mentioned in the backgrounds of the Invention, zwitterionic surfactants show significant advantages relative to either cationic or anionic surfactants due to zwitterions have both positive and negative electric charges in their structure, which increases the possibility to interact with rock surfaces having both positive and negative charges in contrast to the surfactants having only one type of charge.

In many fields at international level, it is shown the case of heterogeneous lithologies, which hinder the enhanced recovery process by wettability change; in this case it is required the use of wettability modifiers to be effective in contact with different types of rock such as limestone, dolomite, sandstone, quartz or heterogeneous lithologies, even in the presence of brines having high content of divalent ions such as calcium, magnesium, barium and strontium, and under high temperature and high pressure in enhanced oil recovery processes to increase oil production.

At the other hand, the branching effect on tensoactive agents is reported in the scientific article "Interfacial Tension Behavior of Mono-Isomeric Phenyltetradecane Sulfonates" (Energy Sources 2005, 27, 1013-1018), which mentions that the surface tension of a system can be modified by manipulating the surfactant molecular structures, and in chain isomers the surface tension decreases as a symmetry in the branches is reached. From the above, it is derived symmetrical branching in geminal zwitterionic liquids improves the wettability-modifier performance relative to the unbranched structures by generating a reducing effect of the interfacial tension.

From the above data, it is had that the generation of branched geminal zwitterionic liquids shows advantages over conventional surfactants for their application as wettability modifiers in different types of lithologies and under high salinity and high temperature conditions.

At the molecular level, the viscosity reduction is directly related to the dispersion degree of polar molecules constituting the fluid. While these molecules are found more dispersed from themselves, lower will be the magnitude of the interaction forces between them and, therefore, the oil viscosity will be lower. Badger et al. (Badger M. W.; Schobert, H. Viscosity Reduction in Extra Heavy Crude Oils. Carbon, vol. 1, p. 76.6.) carried out a study on the viscosity reduction of extra-heavy oils by using different low-molecular-weight chemicals, finding a correlation between the viscosity-reducing efficiency and the polarity of the dispersant molecule. That is, as the dispersant polarity increases, also the recorded viscosity value increases. This means that in a high-polarity additive, the dipole-dipole forces among their molecules are stronger and, therefore, even though the additive could break the asphaltene-asphaltene aggregates, latter would have a high potential for aggregation, generating a increase but not a reduction of the viscosity. It is worthy to highlight that in this study the employed molecules were low molecular weight and volume, reason by which it was observed a dominant effect of the dipole-dipole interaction. In this sense, it has been reported in literature that increasing the free volume of a specific dispersant of the nonpolar substituent, colloidal stabilization is increased and thus it would be expected a reduction of the intermolecular attraction forces causing the viscosity increase.

Introducing appropriate nonpolar substituents would generate an increased dispersing effect, which in turn would help to reduce the required amount of dispersant or viscosity reducer. In that sense, the introduction of lateral nonpolar groups having high molecular volume within a polar head able to generate great-magnitude attractive intermolecular forces such as the ion-dipole one, presents a high potential to function as a viscosity reducer of heavy crude oils having high content of polar molecules. The branched geminal zwitterionic liquids of the present invention show all molecular characteristics desired from their design to function properly in this type of applications.

In order to demonstrate the above premises, theoretical calculations were performed, where it is simulated the adsorption process of high-molecular-weight polar molecules on the original-water-wet rock surface in order to determine the adsorption energy must be overcome by the wettability-modifier molecule; also, it was simulated the branched-geminal-zwitterionic-liquids adsorption process of the present invention on the same original-water-wet rock in order to determine the adsorption energy and to compare it with the above one, so establishing from the theoretical viewpoint wether the asphaltenes desorption process would be thermodynamically favorable by introducing a wettability modifier belonging to the present invention. The obtained results are described in the following examples:

Example 1

Asphaltene-Calcite Interaction

Figure 5:
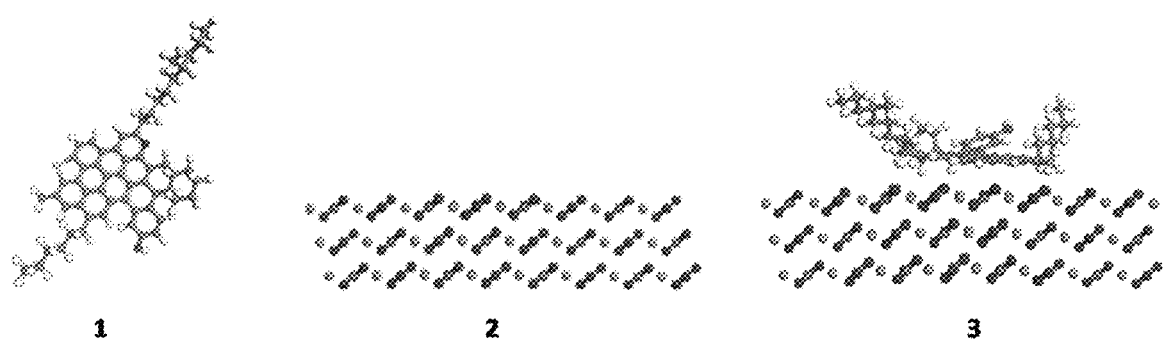
FIG. 5 shows the chemical structure of the asphaltene, calcite surface, and the asphaltene adsorbed on the calcite surface.

By means of computational chemistry, and using quantum methods which employ the Density Functional Theory and the LDA-VWN functional, it was optimized in a water-solvated medium (78.54 dielectric constant) the following molecular systems, shown in FIG. 5: the geometry of an asphaltene-model molecular structure representing the characteristics of a heavy oil from the Marine Region in Mexico (Garcia-Martinez; J.; Tesis de Maestría. 2004; Una aproximación a la estructura molecular de asfaltenos separados de aceites crudos mexicanos; Facultad de Estudios Superiores Cuautitlán de la Universidad Nacional Autónoma de México; México) (1), the calcite ($CaCO_3$)-surface geometry (2), and the geometry of the adsorption product (3) generated from the interaction of the asphaltene-model molecular-structure (1) with calcite ($CaCO_3$) surface (2). The energy results obtained for the adsorption process of the asphaltene molecular-structure model on the calcite ($CaCO_3$) surface are shown in Table 2.

TABLE 2

Energy results obtained for the adsorption of an asphaltene molecular-structure model (1) on the calcite ($CaCO_3$) surface (2), obtained through Density Functional Theory and the LDA-VWN functional in a water-solvated medium.

| Molecule or Complex | Density Functional Theory, LDA-VWN functional | |
|---|---|---|
| | Total energy (kcal/mol) | Interaction energy (kcal/mol) |
| 1 | −1,727,746.029 | −188.63 |
| 2 | −70,629,899.290 | |
| 3 | −72,356,833.960 | |

According to the results of Table 2, it is noted the adsorption of asphaltenes on the calcite surface would be a thermodynamically favorable process, given the negative sign of the interaction energy, which has a magnitude of 188.63 kcal/mol. This example simulates the obtaining of an oil-wet carbonate rock, which is a process experimentally attributed to the oil-polar-compound adsorption on the rock over hundreds and thousands of years. The above interaction energy constitutes the energy barrier that must be overcome by a wettability modifier injected into the reservoir in an enhanced recovery process.

Example 2

Figure 6:
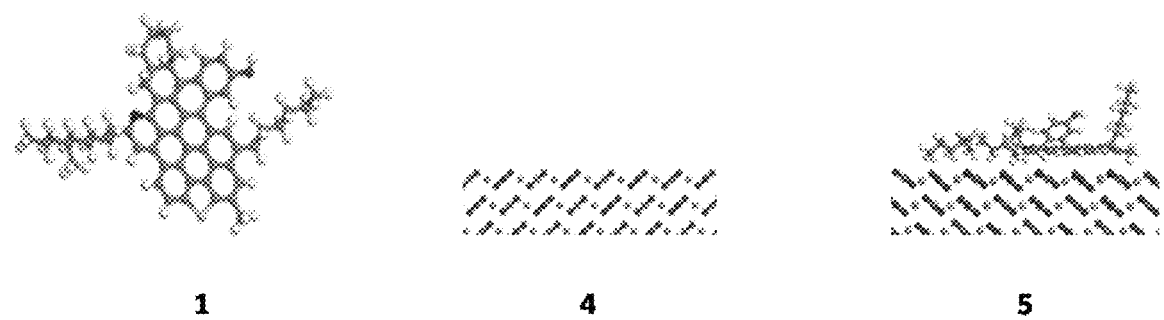
FIG. 6 shows the chemical structure of the asphaltene, dolomite surface, and the asphaltene adsorbed on the dolomite surface.

By means of computational chemistry and using quantum methods which employ the Density Functional Theory and the LDA-VWN functional, it was optimized in a water-solvated medium (78.54 dielectric constant) the following molecular systems, shown in FIG. 6: the geometry of an asphaltene-model molecular structure representing the characteristics of a heavy oil from the Marine Region in Mexico (Garcia-Martinez; J.; Tesis de Maestría. 2004; Una aproximación a la estructura molecular de asfaltenos separados de aceites crudos Mexicanos; Facultad de Estudios Superiores Cuautitlán de la Universidad Nacional Autónoma de México; México) (1), the dolomite ($CaMg(CO_3)_2$)-surface geometry (4), and the geometry of the adsorption product (5) generated from the interaction of the asphaltene-model molecular-structure (1) with dolomite ($CaMg(CO_3)_2$) surface (4). The energy results obtained for the adsorption process of the asphaltene molecular-structure model on the dolomite ($CaMg(CO_3)_2$) surface are shown in Table 3.

TABLE 3

Energy results obtained for the adsorption of an asphaltene molecular-structure model (1) on the dolomite (CaMg (CO$_3$)$_2$) surface (4), obtained through Density Functional Theory and the LDA-VWN functional in a water-solvated medium.

| Molecule or Complex | Density Functional Theory, LDA-VWN functional | |
|---|---|---|
| | Total energy (kcal/mol) | Interaction energy (kcal/mol) |
| 1 | | −178.07 |
| 4 | | |
| 5 | | |

According to the results of Table 3, it is noted the adsorption of asphaltenes on the dolomite surface would be a thermodynamically favorable process, given the negative sign of the interaction energy, which has a magnitude of 178.07 kcal/mol.

Example 3

Figure 7:
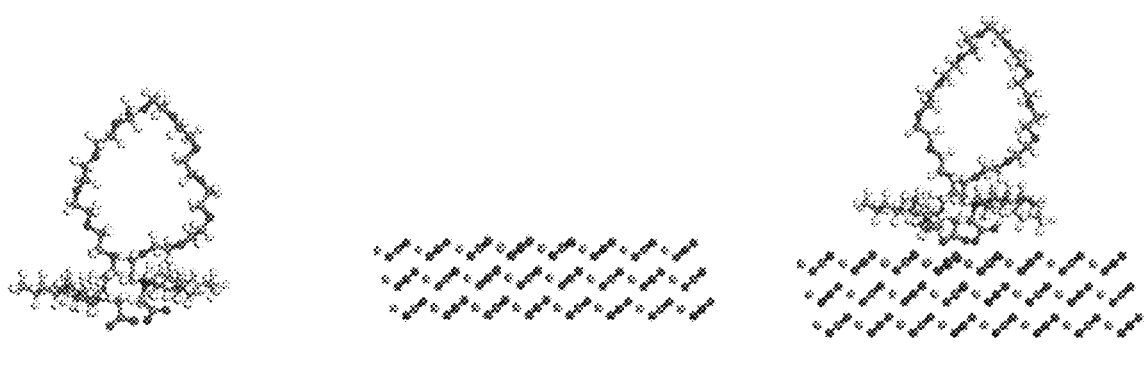
FIG. 7 shows the chemical structure of the branched geminal zwitterionic liquid, calcite surface, and branched geminal zwitterionic liquid adsorbed.

By means of computational chemistry, and using quantum methods which employ the Density Functional Theory and the LDA-VWN functional, it was optimized in a water-solvated medium (78.54 dielectric constant) the following molecular systems, shown in FIG. 7: the geometry of the molecular structure of a branched geminal zwitterionic liquid belonging to the present invention (6), the calcite (CaCO$_3$)-surface geometry (2), and the adsorption product geometry (7) generated from the interaction of the zwitterionic-liquid molecular structure (6) with the calcite (CaCO$_3$) surface (2). The energy results obtained for the adsorption process of the zwitterionic-liquid molecular structure on the calcite (CaCO$_3$) surface are shown in Table 4.

TABLE 4

Energy results obtained for the adsorption process of a branched geminal zwitterionic liquid molecular structure (6) on the calcite (CaCO$_3$) surface (2), obtained through Density Functional Theory and the LDA-VWN functional in a water-solvated medium.

| Molecule or Complex | Density Functional Theory, LDA-VWN functional | |
|---|---|---|
| | Total energy (kcal/mol) | Interaction energy (kcal/mol) |
| 6 | −2,333,700.70 | −294.09 |
| 2 | | |
| 7 | | |

According to the results of Table 4, it is noted the adsorption of the present invention-belonging branched geminal zwitterionic liquid on the calcite surface would be a thermodynamically favorable process, given the negative sign of the interaction energy, which has a magnitude of 294.09 kcal/mol. Moreover, when comparing this last result with the one shown in Table 2 corresponding to the asphaltene-calcite interaction, it is had the zwitterionic liquid-calcite interaction is more favorable, i.e. its energy is lower, so it is confirmed from the theoretical viewpoint that the zwitterionic liquids have the potential to function adequately as wettability modifiers for rocks having high tendency to be oil-wet such as carbonate rocks.

Example 4

Figure 8:
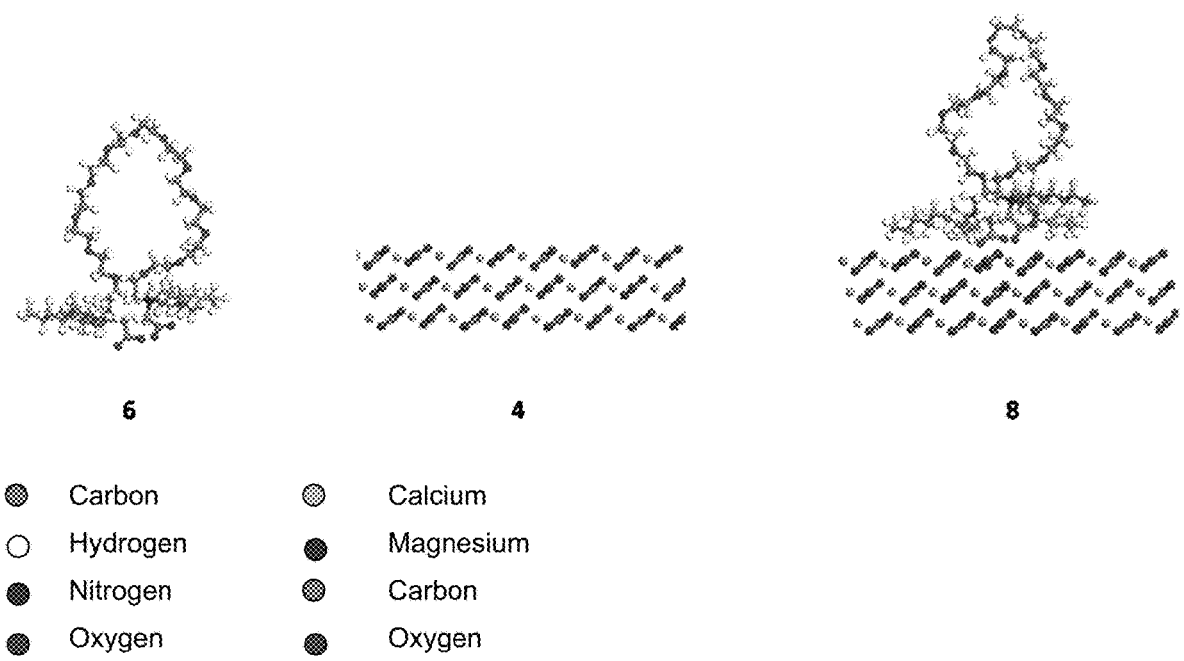
FIG. 8 shows the chemical structure of the zwitterionic liquid, dolomite surface, and branched germinal zwitterionic liquid adsorbed.

By means of computational chemistry, and using quantum methods which employ the Density Functional Theory and the LDA-VWN functional, it was optimized in a water-solvated medium (78.54 dielectric constant) the following molecular systems, shown in FIG. 8: the geometry of the molecular structure of a branched geminal zwitterionic liquid belonging to the present invention (6), the dolomite (CaMg(CO$_3$)$_2$)-surface geometry (4), and the adsorption product geometry (8) generated from the interaction of the zwitterionic-liquid molecular structure (6) with the dolomite (CaMg(CO$_3$)$_2$) surface (4). The energy results obtained for the adsorption process of the zwitterionic-liquid molecular structure on dolomite (CaMg(CO$_3$)$_2$) surface geometry are shown in Table 5.

TABLE 5

Energy results obtained for the adsorption process of a branched geminal zwitterionic liquid molecular structure (6) on the dolomite (CaMg(CO$_3$)$_2$) surface geometry (4) obtained through Density Functional Theory and the LDA-VWN functional in a water-solvated medium.

| Molecule or Complex | Density Functional Theory, LDA-VWN functional | |
|---|---|---|
| | Total energy (kcal/mol) | Interaction energy (kcal/mol) |
| 6 | −2,333,700.70 | −355.45 |
| 4 | | |
| 8 | | |

According to the results of Table 5, it is noted the adsorption of the present invention-belonging branched geminal zwitterionic liquid on the dolomite surface would be a thermodynamically favorable process, given the negative sign of the interaction energy, which has a magnitude of 355.45 kcal/mol. Moreover, when comparing this last result with the one shown in Table 3 corresponding to the asphaltene-calcite interaction, it is had the zwitterionic liquid-dolomite interaction is more favorable, i.e. its energy is lower, so it is confirmed from the theoretical viewpoint that the zwitterionic liquids have the potential to function adequately as wettability modifiers for rocks having tendency to be oil-wet such as carbonate rocks.

Example 5

Asphaltene-Asphaltene Interaction

Figure 9:
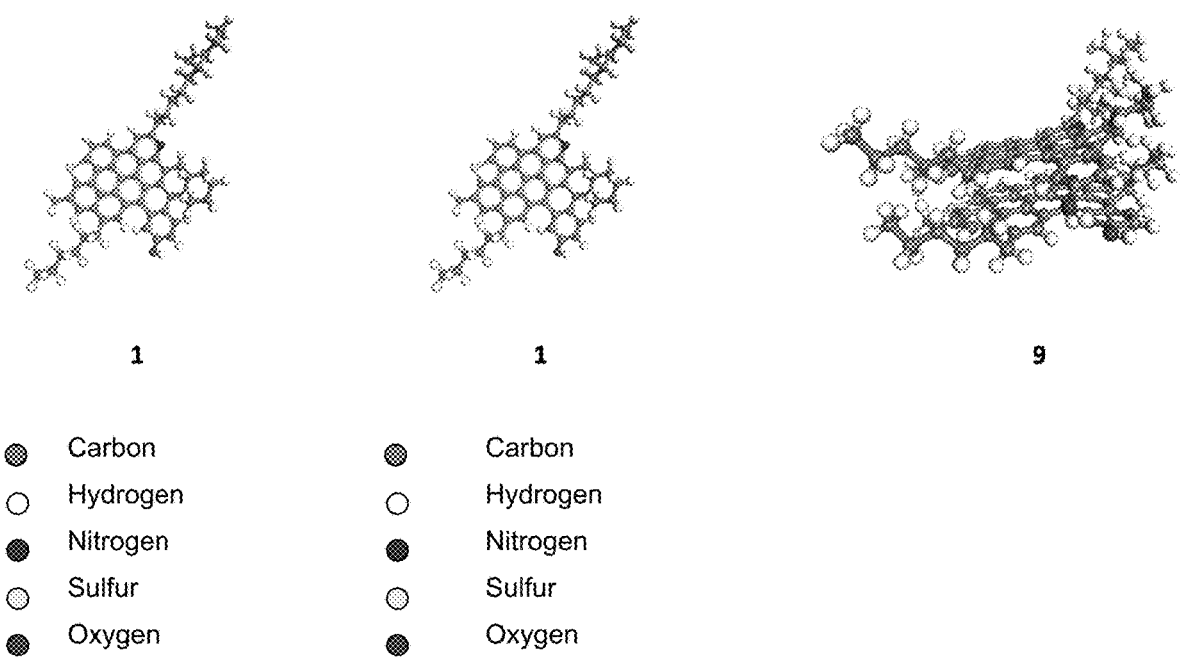
FIG. 9 shows the geometry of two asphaltene-model molecular structures and the geometry of the aggregation between two asphaltene molecular structures.

By means of computational chemistry, and using quantum methods which employ the Density Functional Theory and the LDA-VWN functional, it was optimized in a water-solvated medium (78.54 dielectric constant) the following molecular systems, shown in FIG. 9: the geometry of two asphaltene-model molecular-structures representing the characteristics of a heavy oil from the Marine Region in Mexico (García-Martínez; J.; Tesis de Maestría. 2004) (1), and the geometry of the interaction product or aggregation between two asphaltene molecular structures (9). The energy results obtained for the aggregation process between the two asphaltene molecular-structure models are shown in Table 6.

TABLE 6

Energy results obtained for the aggregation process of two asphaltene molecular-structure models obtained through Density Functional Theory and the LDA-VWN functional in a water-solvated medium.

| Molecule or Complex | Density Functional Theory, LDA-VWN functional | |
|---|---|---|
| | Total energy (kcal/mol) | Interaction energy (kcal/mol) |
| 1 | −1,727,746.029 | −250.81 |
| 1 | −1,727,746.029 | |
| 9 | −3,455,742.87 | |

Example 6

Zwitterionic Liquid-Asphaltene Interaction

By means of computational chemistry, and using quantum methods which employ the Density Functional Theory and the LDA-VWN functional, it was optimized in a water-solvated medium (78.54 dielectric constant) the following molecular systems, shown in (13): the geometry of an asphaltene-model molecular structure representing the characteristics of a heavy oil from the Marine Region in Mexico (García-Martinez; J.; Tesis de Maestría. 2004) (1), the geometry of the molecular structure of a branched geminal zwitterionic liquid belonging to the present invention (6), and the interaction-product geometry (10) of the asphaltene-model structure molecular (1) and the invention-belonging branched-geminal-zwitterionic-liquid molecular structure (6). The energy results obtained for the interaction process of the asphaltene-model structure molecular and with the invention-belonging branched geminal zwitterionic liquid are shown in Table 7.

TABLE 7

Energy results obtained for the interaction process of the asphaltene-model structure molecular (1) with an invention-belonging branched geminal zwitterionic liquid (6), obtained through the Density Functional Theory and the LDA-VWN functional in a water-solvated medium.

| Molecule or Complex | Density Functional Theory, LDA-VWN functional | |
|---|---|---|
| | Total energy (kcal/mol) | Interaction energy (kcal/mol) |
| 1 | — | −188.63 |
| 6 | −2,333,700.700 | |
| 9 | − | |

2) Synthesis of Branched Geminal Zwitterionic Liquids

Once completed the molecular design stage, the selected branched geminal zwitterionic liquids are synthesized at the laboratory level and subsequently evaluated to confirm the design information, and thereafter the performance of the present-invention-belonging branched geminal zwitterionic liquids was evaluated experimentally as wettability modifiers and viscosity reducers in different rock and oil types under high salinity and high temperature conditions.

The branched geminal zwitterionic liquids based on either bis-N,N,dialkyl-N-polyether-betaine or bis-N,N,dialkenyl-N-polyether-betaine or bis-N,N,dicycloalkyl-N-polyether-betaine or bis-N,N,diaryl-N-polyether-betaine, which are object of the present invention, are prepared according to the following synthesis scheme:

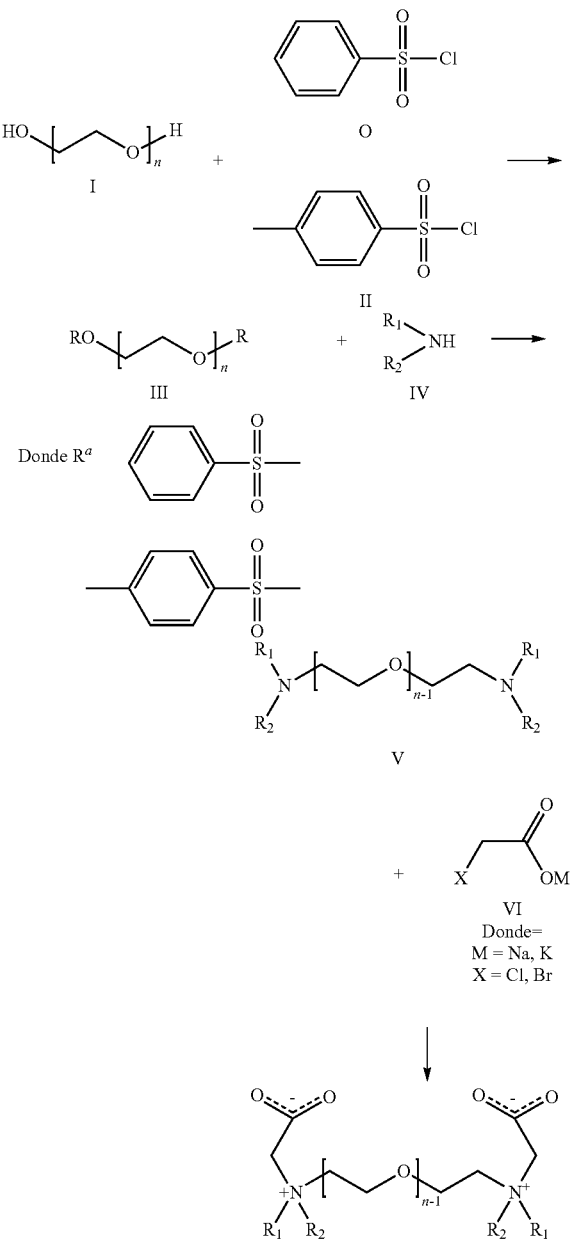

(13) Synthesis Scheme for Obtaining the Branched Geminal Zwitterionic Liquids of Structural Formula VII The first step consists in to react polyethylene glycols of formula I, which are derived from ethylene oxide with two hydroxyl groups, one at the end and the other at the beginning of the polymer chain, and whose molecular weight is found in the range from 100 to 20,000 g/mol; with either p-toluensulfonyl chloride or tosyl chloride; where the reaction is carried out at a molar relationship from 1:1 to 1:4 between the polyethylene glycols of formula I and the either p-toluensulfonyl chlorides or tosyl chlorides, preferably from 1:1.5 to 1:2.8, with a sodium potassium or cesium alkaline base, preferably sodium hydroxide; using as solvent either water, tetrahydrofuran, clororoform, acetonitrile or mixtures thereof, during a reaction time from 1 to 12 hours, preferably from 3 to 8 hours, and at a temperature from 0 to 25° C., preferably from 5 to 20° C., in order to form compounds of formula III.

The second stage consists of reacting the compounds of formula III through a nucleophilic substitution with secondary amines of formula IV whose R1 and R2 may be alkyl or alkenyl, linear or branched chains, preferably from 1 to 30 carbon atoms, or cycle alkyl or aryl groups, preferably from 5 to 12 carbon atoms and wherein the reaction is carried out at a molar ratio between the compounds of formula III and IV from 1:1.5 to 1:4, preferably from 1:1.8 to 1:2.6, under the presence of solvents such as acetonitrile, chloroform, dimethylformamide, dimethylsulfoxide, acetone or short-chain alcohols, during a reaction time from 6 to 60 hours, preferably 36 hours, and at a temperature from 50 to 150° C., in order to obtain tertiary amines of formula V.

The third stage consists in the reaction between the compounds of formula V and halogenated alpha acids such as the chloroacetic or bromineacetic acids or its salts of formula VI, in a molar ratio from 1:1.5 to 1:4, preferably from 1:1.8 to 1:2.6, the reaction is carried out in the presence of solvents such as water, short-chain alcohols, aromatics and inert hydrocarbon, preferably water; the reaction time, the temperature and the pressure depend on the compound structure of formula V and VI. Usually the reaction time varies from 6 to 72 hours, preferably 6 to 48 hours, the temperature from 40 to 180° C., preferably 80 to 130° C., and the pressure is generally atmospheric, in order to obtain compounds of formula VII; based on either bis-N,N,dialkyl-N-polyether-betaine or bis-N, N, dialkenyl-N-polyether-betaine or bis-N,N,dicycloalkyl-N-polyether-betaine or bis-N,N,diaryl-N-polyether-betaine.

Below it is described some practical examples for branched-geminal-zwitterionic-liquids obtaining, in order to have a better understanding of the present invention, without this limits its scope.

Example 7

Preparation of the Branched Geminal Zwitterionic Liquid (Product 1).

As a first stage, in a 500 ml round bottom balloon flask containing 59 g of an aqueous solution with 17 wt % of sodium hydroxide (10 g), it was added 50 g of polyethylene glycol whose average molecular-weight number is 600 g/mol, and the mixture was stirred during 20 minutes. Then, at room temperature (25° C.) and atmospheric pressure it was added very slowly 87 g of a solution of tosyl chloride at 40 wt % (34.8 g) in tetrahydrofuran, keeping the temperature below 25° C. throughout the whole addition. Once the addition is completed, the reaction mixture was stirred for about one hour at room temperature and atmospheric pressure. Then, it was made from the reaction mixture an extraction of the organic phase and the solvent was evaporated at reduced pressure, obtaining 74 g of product A (polyether ditosylate) as a yellow viscous transparent liquid.

In a 500 ml balloon flask equipped with a magnetic stirrer, condenser and thermometer it was added 35.4 g (0.146 mol) of dioctylamine, 74 g of Product A (0.081 mol), 56.5 g (0.4 mol) of potassium carbonate and 200 g of acetonitrile. The reaction mixture was stirred vigorously at reflux temperature and atmospheric pressure during 8 hours.

After the reaction time ended, it was carried out an extraction of the organic phase and the solvent was evaporated at reduced pressure, obtaining 68 g of the product B as an amber viscous liquid.

As the next stage, in a 1000 ml balloon flask equipped with a condenser, magnetic stirrer and thermometer, it was put 68 g (0.065 mol) of Product B and it was added a solution of 15.1 g (0.13 mol) of sodium chloroacetate in 750 g of water.

The reaction mixture was stirred vigorously at a reflux temperature and atmospheric pressure during 24 hours.

Once the reaction time ended, the aqueous phase was separated and evaporated under reduced pressure. The dry product was washed with chloroform to remove through filtration the salts present. The organic fraction was evaporated under reduced pressure to obtain 63 g of zwitterionic liquid as an amber viscous liquid called Product 1.

The spectroscopic characteristics of Product 1 are the shown below:

Representative FTIR bands of (cm$^{-1}$): 2924, 2867, 1632, 1466, 1349, 1298, 1100, 947 and 747.

Representative $^1$H NMR chemical shifts (in CDCl3), 200 MHz, δ (ppm): 3.84, 3.57, 3.11, 2.92, 1.62, 1.19 and 0.80.

Representative $^{13}$C NMR chemical shifts (in CDCl3), 50 MHz, δ (ppm): 176.3, 70.4, 66.0, 52.8, 51.6, 31.5, 28.9, 26.7, 22.4 y 13.9.

Example 8

Preparation of the Branched Geminal Zwitterionic Liquid (Product 2).

For this example, it was used the Product A described in the Example 7.

As a second reaction stage, in a 500 ml balloon flask equipped with a condenser, magnetic stirrer and a thermometer, it was put 51.9 g (0.146 mol) of didodecylamine, 74 g of Product A (0.081 mol), 56.5 g (0.4 mol) of potassium carbonate and 200 g of acetonitrile. The reaction mixture was stirred vigorously at reflux temperature and atmospheric pressure during 8 hours.

When the reaction time ended, the organic phase was extracted and the solvent evaporated at reduced pressure to obtain 82 g of product C as an amber viscous liquid.

As the third reaction stage, in a 1,000 ml balloon flask equipped with a condenser, a magnetic stirrer and a thermometer, it was put 82 g (0.065 mol) of Product C and it was added a solution of 15 g (0.129 mol) of sodium chloroacetate in 750 g of water. The reaction mixture was stirred vigorously at a reflux temperature and atmospheric pressure during 36 hours.

When the reaction time ended, the aqueous phase was separated and evaporated under reduced pressure. The dry product was washed with chloroform to remove through filtration the salts present. The organic fraction was evaporated under reduced pressure obtaining 75 g of zwitterionic liquid as an amber viscous liquid called Product 2.

The spectroscopic characteristics of Product 2 are the shown below:

Representative FTIR bands (cm$^{-1}$): 2926, 2865, 1634, 1465, 1345, 1292, 1102, 944 and 748.

Representative $^1$H NMR chemical shifts (in CDCl3), 200 MHz, δ (ppm): 3.91, 3.60, 3.23, 3.07, 1.71, 1.22 and 0.84.

Representative $^{13}$C NMR chemical shifts (in CDCl3), 50 MHz, δ (ppm): 176.2, 70.4, 65.6, 52.9, 51.8, 31.8, 29.4, 29.3, 29.2, 26.7, 23.1 and 22.6

Example 9

Preparation of the Branched Geminal Zwitterionic Liquid (Product 3).

For this example, it was used the Product A described in the Example 7.

In a 500 ml balloon flask, equipped with a condenser, a magnetic stirrer and a thermometer, it was put 27.2 g (0.147 mol) of dihexylamine, 74 g of Product A (0.081 mol), 55 g (0.4 mol) of potassium carbonate and 200 g of acetonitrile. The reaction mixture was stirred vigorously at reflux temperature and at atmospheric pressure during eight hours.

When the reaction time ended, the organic phase was extracted and the solvent evaporated at reduced pressure, obtaining 65 g of product D as an amber viscous liquid.

As the next reaction stage, in a 1000 ml balloon flask equipped with a condenser, a magnetic stirrer and a thermometer, it was put 65 g (0.07 mol) of Product D and it was added a solution of 16.2 g (0.14 mol) of sodium chloroacetate in 750 g of water.

The reaction mixture was stirred vigorously at a reflux temperature and at atmospheric pressure during 24 hours.

When the reaction time ended, the aqueous phase was separated and evaporated under reduced pressure. The dry product was washed with chloroform to remove through filtration the salts present. The organic fraction was evaporated under reduced pressure, obtaining 60 g of zwitterionic liquid as an amber viscous liquid called Product 3.

The spectroscopic characteristics of Product 3 are the shown below:

Representative FTIR bands of (cm$^{-1}$): 2923, 2865, 1631, 1462, 1345, 1295, 1101, 945 y 743.

Representative $^1$H NMR chemical shifts (in CDCl3), 200 MHz, δ (ppm): 3.87, 3.61, 3.15, 2.93, 1.63, 1.21 and 0.90.

Representative $^{13}$C NMR chemical shifts (in CDCl3), 50 MHz, δ (ppm): 176.2, 70.2, 65.7, 52.6, 51.7, 31.3, 29.1, 25.7, 21.4 and 14.1.

Example 10

Preparation of the Branched Geminal Zwitterionic Liquid (Product 4).

As the first stage, in a 500 ml round bottom balloon flask, containing 23.3 g of an aqueous solution with 34 wt % of sodium hydroxide (9.34 g), it was added 40 g of polyethylene glycol whose average molecular-weight number is 600 g/mol, and the mixture was stirred during 20 minutes. Then, at room temperature (25° C.) and atmospheric pressure (585 mmHg) it was added very slowly 72.78 g of a solution of benzene sulfonyl chloride at 30 wt % (24.74 g) in chloroform, keeping the temperature below 25° C. throughout the whole addition. Once the addition is complete, the reaction mixture was stirred for about four hours at room temperature and atmospheric pressure. Then, it was made from the reaction mixture an extraction of the organic phase, obtaining 95 g of a solution of polyether bencensulfonate in chloroform.

As a second stage, in a 500 ml balloon flask equipped with a condenser, a magnetic stirrer and a thermometer, it was put 17.3 g of dioctylamine, 17.4 g of potassium carbonate and 95 g of the solution obtained in the previous stage which contains 38 g of polyether bencensulfonate. The reaction mixture was stirred vigorously at reflux temperature and atmospheric pressure during 40 hours.

At the end of reaction time, the organic phase was extracted and the solvent was evaporated at reduced pressure, obtaining 53 g of Product VII as an amber viscous liquid.

As a third stage, in a 1000 ml balloon flask equipped with a condenser, a magnetic stirrer and a thermometer, it was put 53 g of Product VII and it was added a solution of 9.84 g of sodium chloroacetate in 700 g of water.

The reaction mixture was stirred vigorously at a reflux temperature and at atmospheric pressure during 24 hours.

Once the reaction time ended, the aqueous phase was evaporated under reduced pressure. The dry product was washed with chloroform to remove through filtration the salts present. The organic fraction was evaporated under reduced pressure, obtaining 60 g of the zwitterionic liquid as an amber viscous liquid called Product 4.

The spectroscopic characteristics of Product 4 are the shown below:

Representative FTIR bands of (cm$^{-1}$): 2924, 2853, 1631, 1465, 1349, 1297, 1099, 947 and 746.

Representative $^1$H NMR chemical shifts (in CDCl3), 200 MHz, δ (ppm): 3.83, 3.57, 3.11, 2.92, 1.63, 1.19 and 0.80.

Representative $^{13}$C NMR chemical shifts (in CDCl3), 50 MHz, δ (ppm): 177.5, 70.3, 66.0, 52.8, 51.6, 31.5, 28.9, 26.7, 22.3 and 13.9.

3) Performance Testing on the Branched Geminal Zwitterionic Liquids as Wettability Modifiers For the evaluation of the wettability-modifying properties of the zwitterionic liquids on rocks such as limestone, dolomite, sandstone, quartz or heterogeneous lithologies, under the presence of brine having high divalent-ions content like calcium, magnesium, barium and strontium, techniques for measuring oil-brine interfacial tension were used allowing to check that the branched geminal zwitterionic liquids of the present invention do not work through a mechanism of reducing interfacial tension down to ultralow values and, therefore, do not generate emulsions nor microemulsions. The interfacial tension there is between the injection water (displacing fluid) and the crude oil (oil) is an actor of great importance within enhanced oil recovery processes, since is directly related to the facility to displace the crude oil trapped in the porous media. Traditionally, surfactants are introduced to the injection water in order to reduce the original water-oil tension down to orders around $10^{-1}$ or $10^{-2}$ N/m. However, the interfacial-tension reduction down to low or ultralow values generates the formation of very-stable emulsions or microemulsions, which affect the oil characteristical properties and obstruct or preclude further oil processing.

At the other hand, the recovery factor by spontaneous-imbibition process on limestone cores within Amott cellls was determined in order to evaluate the wettability-modifiers efficiency of the present invention and to compare it relative to a reference system which does not have the presence of the chemical. For evaluations it was selected cores of limestone, which is composed mainly of calcium carbonate, because it is a rock showing a strong adsorption of polar organic oil compounds and, therefore, is the most severe case for a wettability modifier and then it would guarantee that this chemical-agents type would function adequately for other rock type having less tendency to be oil-wet.

Below it is described both the procedures for each test and the obtained results:

Example 11

Determination Test of the Oil/Brine Interfacial Tension.

This test consists in rotating a capillary tube containing two immiscible liquids inside, where the lightest liquid is injected in a much-less volume ratio than the densest one to form a drop. The tube rotates around its axis in such a manner the drop undergoes a centrifugal force toward the tube walls while simultaneously the interfacial-tension force between the liquids tends to decrease the contact surface between them. The drop geometry reaches stability when the centrifugal force generated by rotation is balanced with the interfacial-tension force. At this way, the interfacial tension between two immiscible fluids (liquid-liquid, gas-liquid, etc.) can be determined from the drop radius in the breakeven according to the following equation:

$$\gamma = \frac{1}{4} \Delta \rho w^2 r^3$$

where r is the drop radius, ω is the angular speed of the tube and Δρ is the density difference between the two immiscible fluids at the test temperature.

The tensiometer used for the evaluations was a Krüss spinning-drop tensiometer, model SITE 100, having a $10^{-6}$-10 mN/m measuring range. It comprises of a glass capillary tube of 3.5 mm internal diameter, which is placed horizontally and fastened to a platform with a variable tilt angle. The capillary-tube body is immersed in an external glass tube that functions as a thermoregulation jacket when it is filled by oil mineral at an operating range from 0 to 100° C.

For the interfacial-tension measurement by the spinning-drop method, it was put 10 μL of oil (lightest fluid) within the capillary tube which is filled with brine (densest liquid) at a temperature of 20° C. The tube rotation speed is fixed at value generating a ratio of at least 1:4 between the radius and the length of the oil drop. It is determined the drop radio and then the tension value is obtained from the above equation.

Example 12

Results of the Connate-Water/Light-Oil Interfacial Tension

It was performed the interfacial-tension determination between connate water and crude oil, whose characteristics are shown by Table 8 and Table 9, respectively. Also, it was determined the connate-water/light-oil interfacial tensions for water samples additivated with different concentrations of branched geminal zwitterionic liquid (Product 1). Results are shown at Table 10.

TABLE 8

| Physical-chemistry analysis of the connate water 1. | | | | |
|---|---|---|---|---|
| Physical properties | | | | |
| Temperature | 20° C. | | | |
| pH | 7.65 | @ 20° C. | | |
| Density | 1.0043 | $g/cm^3$ @ 20° C. | | |
| Conductivity | | μS/cm @ 20° C. | | |
| Turbidity | 4 FTU | | | |
| Chemical properties | | | | |
| Cations | (mg/L) | (meq/L) | Anions | (mg/L) | (meq/L) |
| Sodium ($Na^+$) | 1703.66 | 74.116 | Chlorides ($Cl^-$) | 3200.00 | 90.260 |
| Potassium ($K^+$) | — | — | Sulphates ($SO_4^=$) | 350.00 | 7.287 |
| Calcium ($Ca^{++}$) | 416.00 | 20.758 | Carbonates ($CO_3^=$) | 0.00 | 0.00 |
| Magnesium ($Mg^{++}$) | 106.95 | 8.799 | Bicarbonates ($HCO_3^-$) | 405.04 | 6.638 |
| Iron ($Fe^{++}$) | 0.06 | 0.002 | Hydroxides ($OH^-$) | — | — |
| Manganese ($Mn^{++}$) | — | — | Nitrites ($NO_2^-$) | — | — |
| Barium ($Ba^{++}$) | 35.00 | 0.510 | Nitrates ($NO_3^-$) | — | — |
| Strontium ($Sr^{++}$) | — | — | Phosphates ($PO_4^{-3}$) | — | — |
| Total: | 2261.88 | 104.186 | Total: | 3955.04 | 104.186 |
| Dissolved and suspended solids | | | | |
| | (mg/L) | | | (mg/L) |
| Total solids | — | Total hardness as $CaCO_3$ | | 1,480.00 |
| Total dissolved solids (TDS) | 6,216.92 | Calcium hardness as $CaCO_3$ | | 1,040.00 |
| Total dissolved solids (SST) | — | Magnesium hardness as $CaCO_3$ | | 440.00 |
| Fats and oils | — | Alkalinity to the "F" as $CaCO_3$ | | 0.00 |
| Soluble silica | — | Alkalinity to the "M" as $CaCO_3$ | | 332.00 |
| Ferric oxide | — | Salinity as NaCl | | 5,275.00 |
| Acidity as | — | Stability Index | | 0.28810 |
| | | Tendency | | Encrusting |

TABLE 9

SARA analysis data, acid and basic total number of light oil B.

| Oil | SARA | | | | Total Acid Number (TAN) | Total Basic Number (TBN) |
| --- | --- | --- | --- | --- | --- | --- |
| | Saturated | Aromatic | Resins | Asphalt-enes | | |
| Light oil | 30.68 | 28.62 | 39.35 | 1.32 | 0.21 | 1.7 |

TABLE 10

Results of the connate-water/light-oil interfacial tension at different concentrations of the Product 1.

| Concentration of zwitterionic liquid (mg/L) | Interfacial tension (mN/m) |
| --- | --- |
| 0 | 12.2 |
| 50 | 5.94 |
| 80 | 4.08 |
| 200 | 4.08 |
| 400 | 4.08 |
| 600 | 4.08 |

From the results of Table 10 it can be noted that the addition of zwitterionic liquid to connate water gradually decreases the water/light-oil interfacial tension without achieving low or ultra-low values that would be indicative of the formation of stable either emulsions or microemulsions, respectively. Besides, the moderate decrease degree of the interfacial tension becomes helpful to promote the oil recovery.

Example 13

Determination of the Oil Recovery Factor by Spontaneous Imbibition Process in Limestone Cores within Amott Cells The testing method consists in to measure the amount of crude oil recovered from initially-oil-saturated carbonate-rock cores through spontaneous imbibition processes produced by water, within Amott cells at constant temperature and atmospheric pressure.
Elements required for the test:
Amott cells.
Controlled-temperature recirculation device.
Limestone cores with 3.81 cm diameter and 7 cm long, and known permeabilities and porosities.
Photographic camera.
Crude oil.
High-salinity connate water.
Analytical balance.
Soxhlet-extraction glass equipment.
Glass volumetric material.
Convection oven.
Test procedure:
1) The carbonate (dolostone or limestone) or sandstone rock cores, for which it is attempted to perform the study, are subjected to hydrocarbon-extraction processes by using different organic solvents within a Soxhlet system. The extraction processes are carried out continuously, sequentially and under reflux, using as solvents: a) hexane b) xylene, c) chloroform, d) methanol, e) hexane, f) xylene and g) chloroform. The duration of each extraction stage is one day and the total process time is 7 days.
2) Determine the absolute helium permeability of the cores, as well as their effective porosity.
3) Dry the rock cores in a stove at a temperature of 100° C. and record the weight once a constant weight is reached.
4) Put the rock cores in contact with dead oil from the reservoir of interest during 5 days at the required temperature of interest and at a pressure of 140±5 psi within an aging cell.
5) Strain the dead-oil-saturated rock cores at room temperature and atmospheric pressure until no dropping is observed. The straining process lasts about 12 hours and a number-200 wire mesh is used for this purpose.
6) Weigh the dead-oil-soaked rock cores and, though weight difference, obtain the amount of oil adsorbed by the porous medium.
7) Prepare 500 mL of the aqueous solution (connate water) to be evaluated at the chemical concentration required in the test.
8) Place the dead-oil-impregnated rock core inside the Amott cell and add carefully 350 mL of the chemical product to be evaluated at the required concentration.
9) Increase the system temperature to the temperature desired to carry out the evaluation of the performance of the chemical or sample under study, and maintain the same during the time at which the recovery factor is intended to be determined under the temperature and salinity conditions.
10) Quantify the amount of oil produced by water-spontaneous-imbibition processes under the study conditions and determine the recovery factor according to the following equation:

$$F = \frac{A_R}{A_O} \times 100$$

Where F is the oil recovery factor, $A_R$ is the amount of recovered oil and $A_O$ is the amount of the original oil adsorbed on the porous media.

Table 11 shows the helium permeability data (in milliDarcys) for the Bedford and Constituciones limestone cores.

TABLE 11

Permeability data of the cores used in the evaluations.

| Core | Permeability (miliDarcys) |
| --- | --- |
| 1 | 120.0 |
| 2 | 10.4 |

The evaluation was carried out for two oil types (light and heavy) from Mexican fields.

Example 14

Evaluation Results of a Spontaneous Imbibition Process by Wettability Change Using a Light Crude Oil.

According to the methodology above described, it was placed within the Amott cells carbonate cores type 1. The carbonate cores type 1 were impregnated with light oil (see Table 9) and put in contact with solutions of the Product 1 in connate water 1 during 11 days at 90° C.

Table 12 shows the recovery data obtained from Amott cells of the branched geminal zwitterionic liquid at concentrations of 250, 500, 1,000 and 2,000 mg/L. Connate water without additive was used as a blank.

Figure 1:
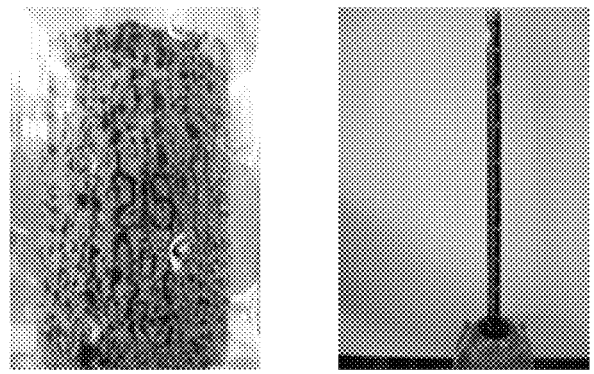
FIG. 1 shows the limestone core saturated by crude oil in contact with the product 1 at different concentrations in imbibition tests within Amott cells: a) 250, b) 500, and c) 1,000 ppm.
Figure 1:
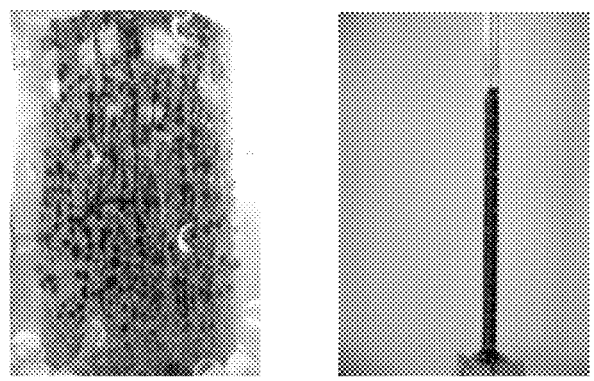
Figure 1:
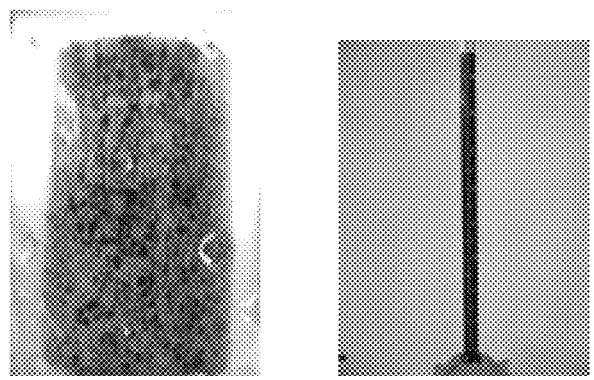
Figure 2:
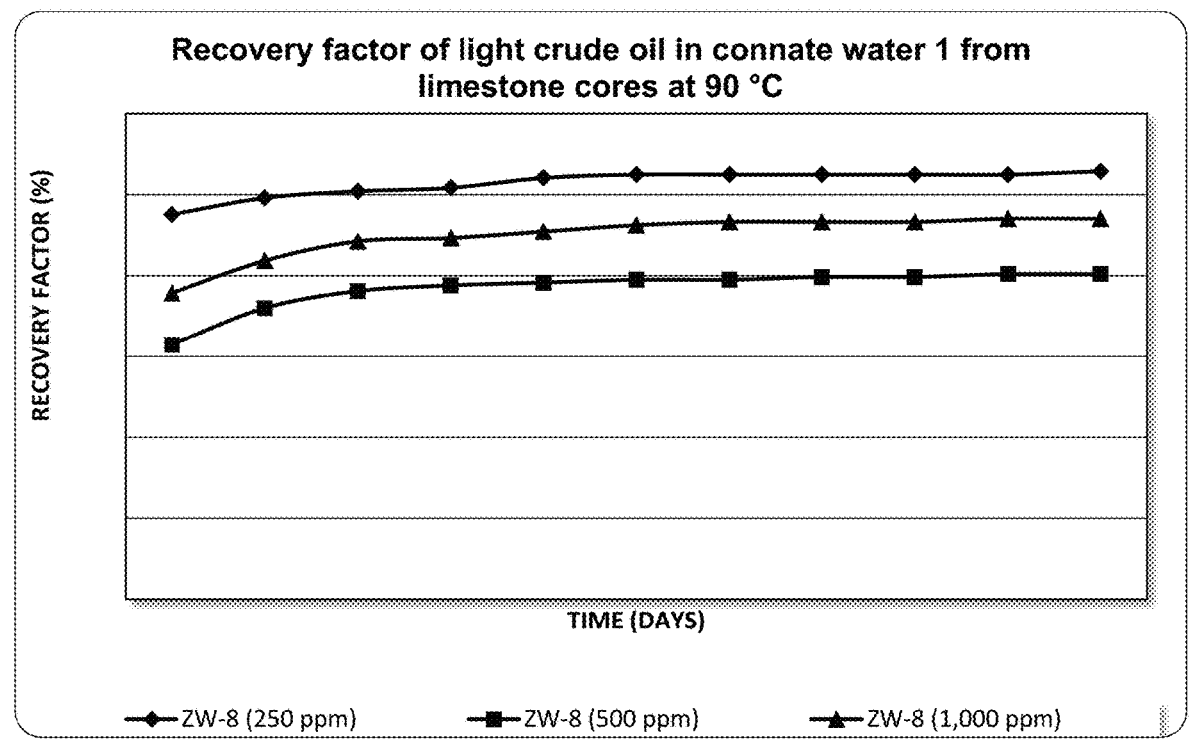
FIG. 2 shows a graph of the recovery factor versus time as a result of the imbibition tests within Amott cells using the product 1.

FIG. 1 shows the Amott cells during the evaluation whereas FIG. 2 shows the graph of the behavior of the recovery factor versus time.

TABLE 12

Light-oil recovery results in Amott cells.

| Concentration of Product 1 (mg/L) | Grams of impregnated oil | Grams of Total Oil Recovered | Percent recovery |
|---|---|---|---|
| 0 | 11.5965 | 0.2188 | 1.88% |
| 250 | 11.9330 | 6.3108 | 52.88% |
| 500 | 13.2869 | 5.3414 | 40.20% |
| 1,000 | 11.9596 | 5.8925 | 49.27% |
| 2,000 | 11.6310 | 5.5389 | 47.62% |

The results in Table 9 indicate that Product 1 is capable to increase the recovery factor by 46% over the chemical-non containing system, even from relatively low concentrations of 250 mg/L or 0.025 wt %. This represents a favorable evidence for its use as a wettability modifier in carbonate-type reservoirs to increase the crude-oil recovery factor.

Example 15

Evaluation Results of a Spontaneous Imbibition Process by Wettability Change Using Heavy Crude Oil According to the methodology above described, it was placed in the Amott cells heavy-oil-impregnated carbonate cores type 1 and 2 put in contact with solutions of the Product 1 or the Product 2 in connate water 2 at concentrations of 500 and 1,000 mg/L.

The crude-oil and connate-water characteristics are shown at Tables 13 and 14.

TABLE 13

Data of SARA analysis and acid and basic total number for the heavy oil.

| Oil | SARA | | | | Total Acid Number (TAN) | Total Basic Number (TBN) |
|---|---|---|---|---|---|---|
| | Saturated | Aromatic | Resins | Asphaltenes | | |
| Heavy oil | 13.4 | 24.76 | 51.01 | 10.44 | 1.83 | 2.12 |

TABLE 14

Physical chemistry analysis for the connate water 1.

| Physical properties | | |
|---|---|---|
| Temperature | 20° C. | |
| pH | 6.68 | @ 20° C. |
| Density | 1.0216 | g/cm$^3$ @ 20° C. |
| Conductivity | 45,600 | µS/cm @ 20° C. |
| Turbidity | 15 FTU | |

| Chemical properties | | | | | |
|---|---|---|---|---|---|
| Cations | (mg/L) | (meq/L) | Anions | (mg/L) | (meq/L) |
| Sodium (Na$^+$) | 11,630.06 | 505,907 | Chlorides (Cl$^-$) | 22,000.00 | 620,540 |
| Potassium (K$^+$) | — | — | Sulphates (SO$_4$=) | 825.00 | 17,177 |
| Calcium (Ca$^{++}$) | 1,976.00 | 98,603 | Carbonates (CO$_3$=) | 0.00 | 0.00 |
| Magnesium (Mg$^{++}$) | 427.86 | 35,197 | Bicarbonates (HCO$_3$-) | 122.00 | 1,999 |
| Iron (Fe$^{++}$) | 0.25 | 0.009 | Hydroxides (OH$^-$) | — | — |
| Manganese (Mn$^{++}$) | — | — | Nitrites (NO$_2$-) | — | — |
| Barium (Ba$^{++}$) | — | — | Nitrates (NO$_3$-) | — | — |
| Strontium (Sr$^{++}$) | — | — | Phosphates (PO$_4$-3) | — | — |
| Total: | 14,034.41 | 639,716 | Total: | 22,947.00 | 639,716 |

| Dissolved and suspended solids | | | |
|---|---|---|---|
| | (mg/L) | | (mg/L) |
| Total solids | — | Total hardness as CaCO$_3$ | 6,700.00 |
| Total Dissolved Solids (TDS) | 36,981.41 | Calcium hardness as CaCO$_3$ | 4,940.00 |
| Total Dissolved Solids (SST) | — | Magnesium hardness as CaCO$_3$ | 1,760.00 |
| Fats and oils | — | Alkalinity to the "F" as CaCO$_3$ | 0.00 |
| Soluble silica | — | Alkalinity to the "M" as CaCO$_3$ | 100.00 |
| Ferric oxide | — | Salinity as NaCl | 36,265.59 |
| Acidity as | — | Stability Index | −0.71714 |
| | | Tendency | Corrosive |

Table 15 shows the data obtained from Amott cells with carbonate cores type 1 and 2 in contact with solutions of branched geminal zwitterionic liquids at concentrations of 500 ppm and 1,000 ppm in connate water 2 used as a blank and using heavy crude oil.

TABLE 15

Heavy-oil recovery results from Amott cells.

| Product | Product Concentration (mg/L) | Core Type | Impregnated-oil grams | Total Oil-Recovered grams | Percent recovery (%) |
|---|---|---|---|---|---|
| — | 0 | 1 | 11.2965 | 0.022 | 0.19 |
| 1 | 500 | 1 | 11.5191 | 1.5995 | 13.89 |
| 1 | 1,000 | 1 | 12.9494 | 3.7822 | 29.21 |
| — | 0 | 2 | 11.6119 | 0.4008 | 3.45 |
| 1 | 1000 | 2 | 14.1636 | 1.9684 | 13.90 |
| 2 | 500 | 1 | 11.4352 | 3.7164 | 32.50 |
| 2 | 1000 | 1 | 11.9243 | 2.9990 | 25.15 |
| 2 | 500 | 2 | 11.7123 | 1.8529 | 15.82 |
| 2 | 1000 | 2 | 12.3531 | 1.3230 | 10.71 |

The obtained results show that branched geminal zwitterionic liquids are able to increase the crude-oil recovery factor in limestone lithologies having variable permeability and containing both light and heavy crude oils.

Example 16

Test to Evaluate the Viscosity Reduction of Oils Having High Content of Polar Fractions The test consists in to determine the viscosity-reduction degree of a heavy crude oil by the addition of branched geminal zwitterionic liquids at different concentrations, as well as the effect of this reduction at different temperatures. The zwitterionic liquid can be added directly to the crude oil at the required concentration, directly comparing in this case the initial viscosity of the oil without chemical versus the viscosity of the oil with chemical at each chemical concentration and selected temperature.

In some cases, it could be desirable to dilute the zwitterionic liquid with some solvent in the sake of an ease operation, and this mixture would be added to crude oil to reduce the viscosity. In order to determine the zwitterionic liquid contribution to the viscosity reduction, the initial viscosity of crude oil (Reference 1) would be measured and then the viscosity of the crude oil additivated with the zwitterionic liquid-diluent mixture (test sample) would be measured. The effective viscosity reduction attributable to the zwitterionic liquid would be the difference among the Reference 1 viscosity subtraction and the test-sample viscosity, according to the following equation:

$$\% \mu_{Reduced-i} = \frac{\mu_{Ref1} - \mu_i}{\mu_{Ref1}}$$

where $\%\mu_{Reduced-i}$ is the effective viscosity, $\mu_{Ref1}$ is the viscosity of the reference oil and $\mu_i$ is the viscosity of the additivated sample.

Test Procedure:

1. It is prepared 1.0 g of 40% W/W of the chemical to evaluate with xylene reagent grade solution. It is weighed 0.4 g of the chemical and 0.6 g of solvent.
2. It is carried out the measurement of the apparent viscosity of the crude oil Reference 1 in a rotary rheometer using a parallel plates geometry and under the following conditions:
   a. Temperature: 25, 40, 50 and 60° C.
   b. Shear rate: 20 s$^{-1}$
   c. Distance between plates: 1 mm
3. Prepare test-sample solutions in 5 mL glass beakers for dosing in each sample according to the following data:

| Sample | Solvent (g) | 40% w chemical solution (g) | Final mass of chemical product (g) | Solution final concentration (wt %) |
|---|---|---|---|---|
| 1 | 0 | 0.4 | 0.4 | 40% |
| 2 | 0.2 | 0.2 | 0.4 | 20% |
| 3 | 0.3 | 0.1 | 0.4 | 10% |

The final concentrations of chemical product will be the following below:

| Sample | Solution concentration (wt %) | Chemical solution (g) | Crude oil (g) | Diluent-Chemical mixture concentration (ppm$_w$) | Chemical concentration (ppm$_w$) |
|---|---|---|---|---|---|
| 1 | 40% | 0.1 | 19.9 | 5000 | 2000 |
| 2 | 20% | 0.1 | 19.9 | 5000 | 1000 |
| 3 | 10% | 0.1 | 19.9 | 5000 | 500 |

4. For the measurements of chemical products (test sample), it is added 0.1 g of chemical solution and 19.9 g of crude oil within a 50 mL glass beaker. It is stirred the solution for 30 minutes and the measurement is performed at the same conditions as those of the Reference 1.
5. For calculate the viscosity-reduction percent of the original oil, it is calculated the viscosity reduction for each obtained point out.

Example 17

Evaluation Results of Heavy-Crude-Oil Viscosity Reduction.

According to the methodology described in Example 15, it was obtained the viscosities of the heavy crude oil without additive and they were compared with the viscosity results of the same crude oil but additivated with different concentrations of the Product 1 of the present invention at 25° C. Subsequently, it was evaluated the viscosity reduction effect of the Product 1 of the present invention at 1,000 ppm for 6 different temperatures in the range from 60 to 90° C. The results of this test are presented in Table 16 and Table 17.

TABLE 16

Evaluation results of heavy crude oil viscosity reduction by addition of the Product 1 at 25° C.

| Temperature (° C.) | Crude oil | Viscosity (cP) | | | | |
| --- | --- | --- | --- | --- | --- | --- |
| | | Crude oil + Product 1 (500 ppm) | Viscosity reduction (%) | Crude oil + Product 1 (1,000 ppm) | Viscosity reduction (%) | Crude oil + Product 1 (2000 ppm) | Viscosity reduction (%) |
| 25 | 38,000 | 23,600 | 37.89 | 16,800 | 55.79 | 26,500 | 30.26 |

According to the results presented at Table 14, it can be observed that the Product 1 of the present invention is highly efficient (>30%) to reduce at 25° C. the viscosity of a heavy crude oil having high content of polar fractions such as asphaltenes and resins, even from a concentration relatively low of 500 ppm (0.05 wt %), and that this efficiency is maximized at 1,000 ppm.

TABLE 17

Evaluation results of the heavy crude oil viscosity reduction by addition of 1,000 ppm of the Product 1 at different temperatures.

| Temperature (° C.) | Crude oil | Viscosity (cP) Crude oil + Product 1 | Viscosity reduction (%) |
| --- | --- | --- | --- |
| 40 | 17,400 | 4,720 | 72.87 |
| 50 | 13,400 | 2,280 | 82.99 |
| 60 | 4,230 | 917 | 78.32 |
| 70 | 3,390 | 777 | 77.08 |
| 80 | 1,930 | 969 | 49.79 |
| 90 | 924 | 606 | 34.42 |

The results shown in Table 15 reveal that Product 1 of the present invention is highly efficient to reduce the viscosity of heavy crude oil having high content of polar fractions, and that this efficiency is maintained by increasing the measurement temperature in the range from 40 at 90° C. This indicates that this type of molecules would function properly to control flow problems at low-temperatures, which are characteristics of the transport and storage operations characteristics, as well as at high-temperatures, which are characteristics of the reservoir in extraction and production processes.

The invention claimed is:

1. A process for obtaining branched geminal zwitterionic liquids based on either bis-N,N-dialkyl-N-polyether-betaine or bis-N,N-dialkenyl-N-polyether-betaine or Bis-N,N-dicycloalkyl-N-polyether-betaine or bis-N,N-diaryl-N-polyether-betaine, having the following molecular structure:

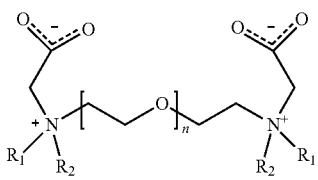

wherein:

$R_1$ is an alkyl or alkenyl, linear or branched chain having from 1 to 30 carbon atoms, or a cycloalkyl or aryl group having from 5 to 12 carbon atoms;

$R_2$ is an alkyl or alkenyl, linear or branched chain having from 1 to 30 carbon atoms, or a cycloalkyl or aryl group having from 5 to 12 carbon atoms;

the label n is an integer from 1 to 500, depending on the molecular weight of used polyether;

the process comprising the following synthetic route:

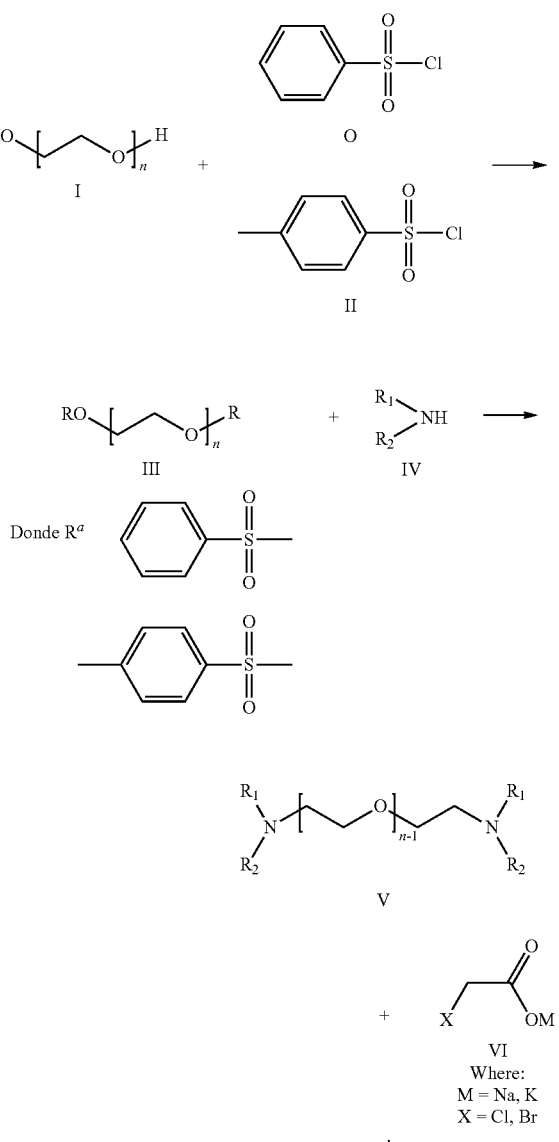

-continued

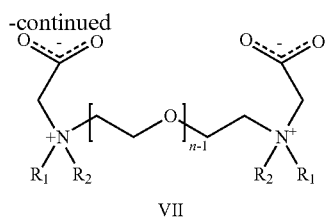

VII wherein the reaction comprises the following stages:
the first step consists of reacting polyethylene glycols of formula I, with either benzenesulfonyl or tosyl chloride of formula II;
the second stage consists of reacting the compounds of formula III via a nucleophilic substitution with secondary amines of formula IV obtaining tertiary amines of formula V;
the third reaction step consists of obtaining compounds of formula VII based on either bis-N,N-dialkyl-N-polyether-betaine or bis-N,N-dialkenyl-N-polyether-betaine or bis-N,N-dicycloalkyl-N-polyether-betaine or bis-N,N-diaryl-N-polyether-betaine which are obtained by reacting the tertiary amines of formula V with halogenated-alpha-acids salts of formula VI.

2. The synthesis process according to claim 1, wherein the polyethyleneglycols of the formula I are derived from ethylene oxide.

3. The synthesis process according to claim 1, wherein the polyethyleneglycol of the formula I have average molecular weight in the range from 100 to 20,000 g/mol.

4. The synthesis process according to claim 1, wherein the reaction between the polyethyleneglycols of formula I and either benzenesulfonyl or tosyl chlorides of formula II is carried out with a molar ratio from 1:1.5 to 1:2.8.

5. The synthesis process according to claim 4, wherein the reaction is carried out in an basic medium composed of either sodium, potassium or cesium hydroxide.

6. The synthesis process according to claim 4, wherein the reaction uses as solvents either water, tetrahydrofuran, chloroform, acetonitrile or mixtures thereof.

7. The synthesis process according to claim 1, wherein in order to obtain the compounds of formula III, the reaction is carried out during a time from 1 to 12 hours.

8. The synthesis process according to claim 1, wherein to obtain compounds of formula III, the reaction is carried out at temperatures from 0 to 25° C.

9. The synthesis process according to claim 1, wherein the reaction is carried out with molar ratio between compounds of formula III and secondary amines of formula IV from 1:1.5 to 1:4.

10. The synthesis process according to claim 1, wherein the reaction to obtain tertiary amines of formula V is carried out under the presence of solvents such as acetonitrile, chloroform, dimethylformamide, dimethyl sulfoxide, acetone or short-chain alcohols.

11. The synthesis process according to claim 1, wherein the reaction to obtain tertiary amines of formula V is carried out during a time from 5 to 60 hours.

12. The synthesis process according to claim 1, wherein the reaction to obtain tertiary amines of formula V is carried out at a temperature from 50 to 150° C.

13. The synthesis process according to claim 1, wherein the reaction between the compounds of formula V and the halogenated alpha acids or their salts of formula VI, is carried out with molar ratio from 1:1.5 to 1:4.

14. The synthesis process according to claim 13, wherein the halogenated alpha acid or its salt is sodium acetate.

15. The synthesis process according to claim 1, wherein the reaction to obtain compounds of formula VII is carried out with or without solvents as water, alcohols, aromatics or hydrocarbon inert solvents.

16. The synthesis process according to claim 1, wherein the reaction time, the temperature and the pressure used to obtain compounds of formula VII, depend on the structure of compounds of formula V and VI.

17. The synthesis process according to claim 16, wherein the reaction varies from 6 to 72 hours.

18. The synthesis process according to claim 16, wherein the reaction temperature ranges from 40 to 180° C.

19. The synthesis process according to claim 16, wherein the pressure ranges from 585 to 760 mmHg.

* * * * *